(12) United States Patent
Wetsch et al.

(10) Patent No.: US 10,974,858 B2
(45) Date of Patent: Apr. 13, 2021

(54) BLADE HOLDER FOR INFLATION AND SEALING DEVICE

(71) Applicant: PREGIS INNOVATIVE PACKAGING LLC, Deerfield, IL (US)

(72) Inventors: Thomas D. Wetsch, St. Charles, IL (US); Paul F. Ostwald, Queensbury, NY (US); William James Watts, Tinley Park, IL (US)

(73) Assignee: Pregis Innovative Packaging LLC, Deerfield, IL (US)

( * ) Notice: Subject to any disclaimer, the term of this patent is extended or adjusted under 35 U.S.C. 154(b) by 535 days.

(21) Appl. No.: 15/472,007

(22) Filed: Mar. 28, 2017

(65) Prior Publication Data

US 2017/0275036 A1    Sep. 28, 2017

Related U.S. Application Data

(60) Provisional application No. 62/314,186, filed on Mar. 28, 2016.

(51) Int. Cl.
  *B65B 61/06*    (2006.01)
  *B31D 5/00*    (2017.01)
  (Continued)

(52) U.S. Cl.
  CPC .......... *B65B 61/06* (2013.01); *A61B 17/3213* (2013.01); *B31D 5/0073* (2013.01);
  (Continued)

(58) Field of Classification Search
  CPC ..... B65B 61/06; B65B 61/10; A61B 17/3213; A61B 2017/32113; B31D 2205/0023;
  (Continued)

(56) References Cited

U.S. PATENT DOCUMENTS 3,881,383 A * 5/1975 Alverth ................. B26D 1/405
                                                          83/308
4,094,217 A * 6/1978 Exline .................... B26D 1/035
                                                          83/368

(Continued)

OTHER PUBLICATIONS

International Search Report and Written Opinion dated Jun. 21, 2017, in PCT/US2017/024604, 11 pages.

*Primary Examiner* — Valentin Neacsu
(74) *Attorney, Agent, or Firm* — Fox Rothschild LLP

(57) ABSTRACT

The present disclosure is directed to an inflatable-cushion inflation and sealing device. The device includes an inflation assembly configured for insertion between first and second overlapping film plies. The inflation assembly includes a fluid conduit configured to direct a fluid in between the plies to form one or more cushions. The fluid conduit includes a nozzle. The inflation assembly includes a cutting member. The cutting member includes a blade holder with a blade and a blade guard mounted thereon. The blade guard has a safety position in which the blade is covered and a retracted position in which the blade is exposed. Installation of the blade holder onto the inflation assembly automatically positions the blade in the working position with the blade guard retracted. Removing the tray from the inflation assembly automatically positions the blade in the safety position by covering the blade with the blade guard.

29 Claims, 16 Drawing Sheets

(51) Int. Cl.
  *B65B 9/15*      (2006.01)
  *B65B 51/22*     (2006.01)
  *B65B 51/02*     (2006.01)
  *B65D 81/05*     (2006.01)
  *A61B 17/3213*   (2006.01)

(52) U.S. Cl.
  CPC .............. *B65B 9/15* (2013.01); *B65B 51/02* (2013.01); *B65B 51/222* (2013.01); *B65B 51/225* (2013.01); *B65D 81/052* (2013.01); *B31D 2205/0023* (2013.01); *B31D 2205/0058* (2013.01)

(58) Field of Classification Search
  CPC .... B31D 2205/0058; B31D 2205/0052; B31D 2205/0047; B31D 2205/0082; B65D 81/052; B65D 81/051
  USPC ....... 53/79, 389.3, 520, 435; 83/37, 56, 343, 83/348, 236, 327, 328, 302, 856–858, 83/284; 493/22, 227, 362, 369, 340; 156/269–271
  See application file for complete search history.

(56) References Cited

U.S. PATENT DOCUMENTS

| | | | | |
|---|---|---|---|---|
| 4,130,037 A * | 12/1978 | Matthews | ............. | B23D 23/00 83/468.2 |
| 4,526,638 A | 7/1985 | Clements et al. | | |
| 4,531,286 A * | 7/1985 | Vito | ............. | B26B 29/02 30/143 |
| 4,675,996 A * | 6/1987 | DuBuque | ............. | B26B 29/02 30/151 |
| 4,744,146 A * | 5/1988 | Schmidt | ............. | B26B 5/001 30/125 |
| 5,417,705 A * | 5/1995 | Haber | ............. | A61B 17/3417 604/164.12 |
| 6,209,286 B1 * | 4/2001 | Perkins | ............. | B31D 5/0073 156/145 |
| 6,928,911 B1 * | 8/2005 | Ratkus | ............. | B26D 1/0006 83/171 |
| 8,128,770 B2 * | 3/2012 | Wetsch | ............. | B29C 65/18 156/147 |
| 8,572,852 B1 * | 11/2013 | Jennings | ............. | B26B 5/001 30/162 |
| 9,168,715 B2 * | 10/2015 | Wetsch | ............. | B31D 5/0073 |
| 2003/0079351 A1 * | 5/2003 | Davis | ............. | B26B 27/005 30/200 |
| 2004/0168558 A1 | 9/2004 | Miyake et al. | | |
| 2006/0218876 A1 * | 10/2006 | Perkins | ............. | B31D 5/0073 53/79 |
| 2006/0219314 A1 * | 10/2006 | Bertram | ............. | B29C 44/182 141/10 |
| 2008/0098534 A1 * | 5/2008 | Yu Chen | ............. | B26B 5/001 7/158 |
| 2010/0024961 A1 * | 2/2010 | Wetsch | ............. | B31D 5/0073 156/147 |
| 2011/0172072 A1 * | 7/2011 | Wetsch | ............. | B31D 5/0073 493/227 |
| 2012/0102754 A1 * | 5/2012 | Garavaglia | ............. | B26B 5/00 30/123 |
| 2012/0102756 A1 * | 5/2012 | Garavaglia | ............. | B26B 5/00 30/143 |
| 2012/0110858 A1 * | 5/2012 | Garavaglia | ............. | B26B 29/02 30/153 |
| 2014/0260872 A1 | 9/2014 | Niizeki et al. | | |
| 2014/0261752 A1 * | 9/2014 | Wetsch | ............. | B65B 41/16 137/223 |
| 2014/0261871 A1 * | 9/2014 | Wetsch | ............. | B31D 5/0073 141/10 |
| 2019/0022878 A1 * | 1/2019 | Wang | ............. | B26B 5/003 |

* cited by examiner

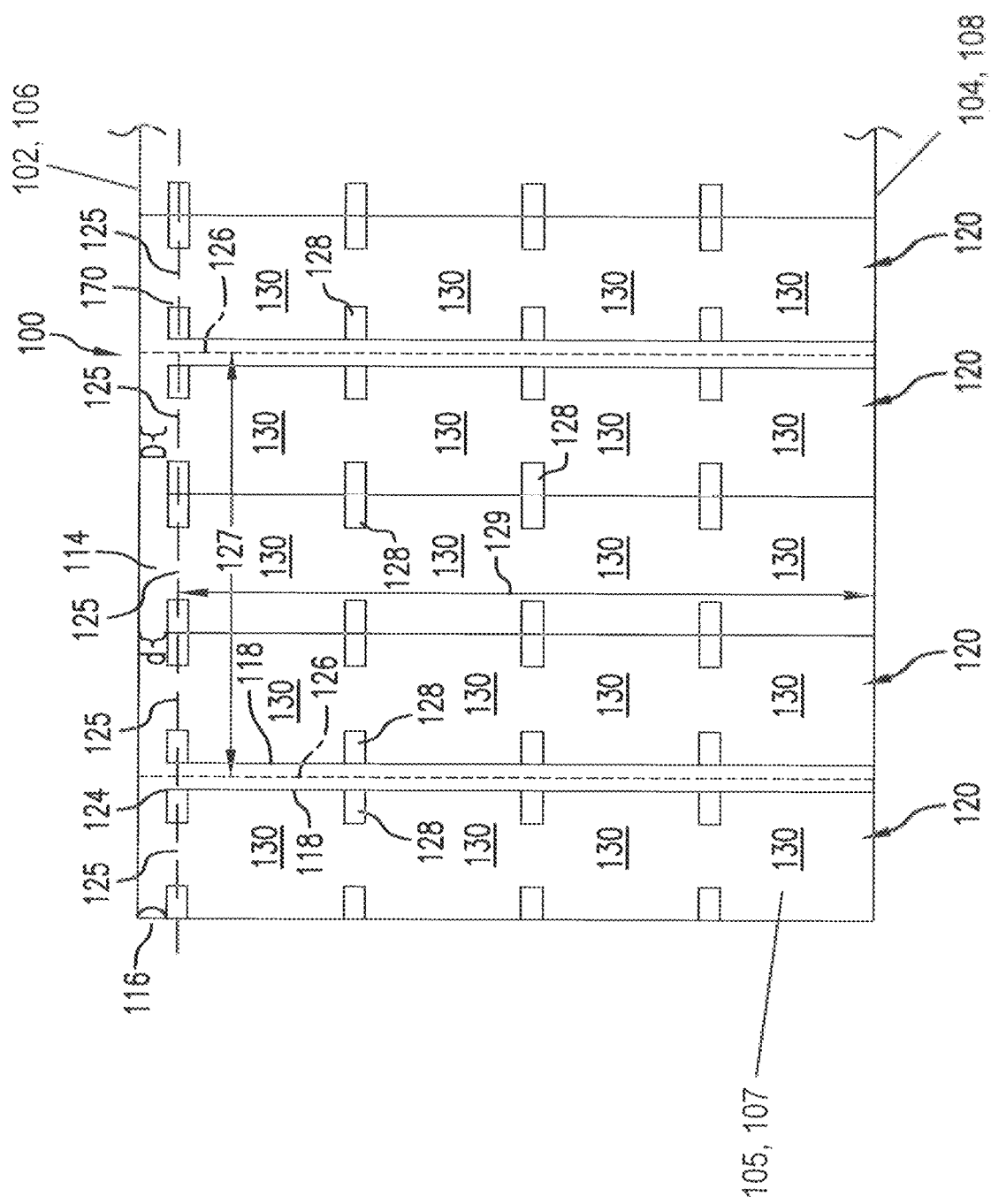

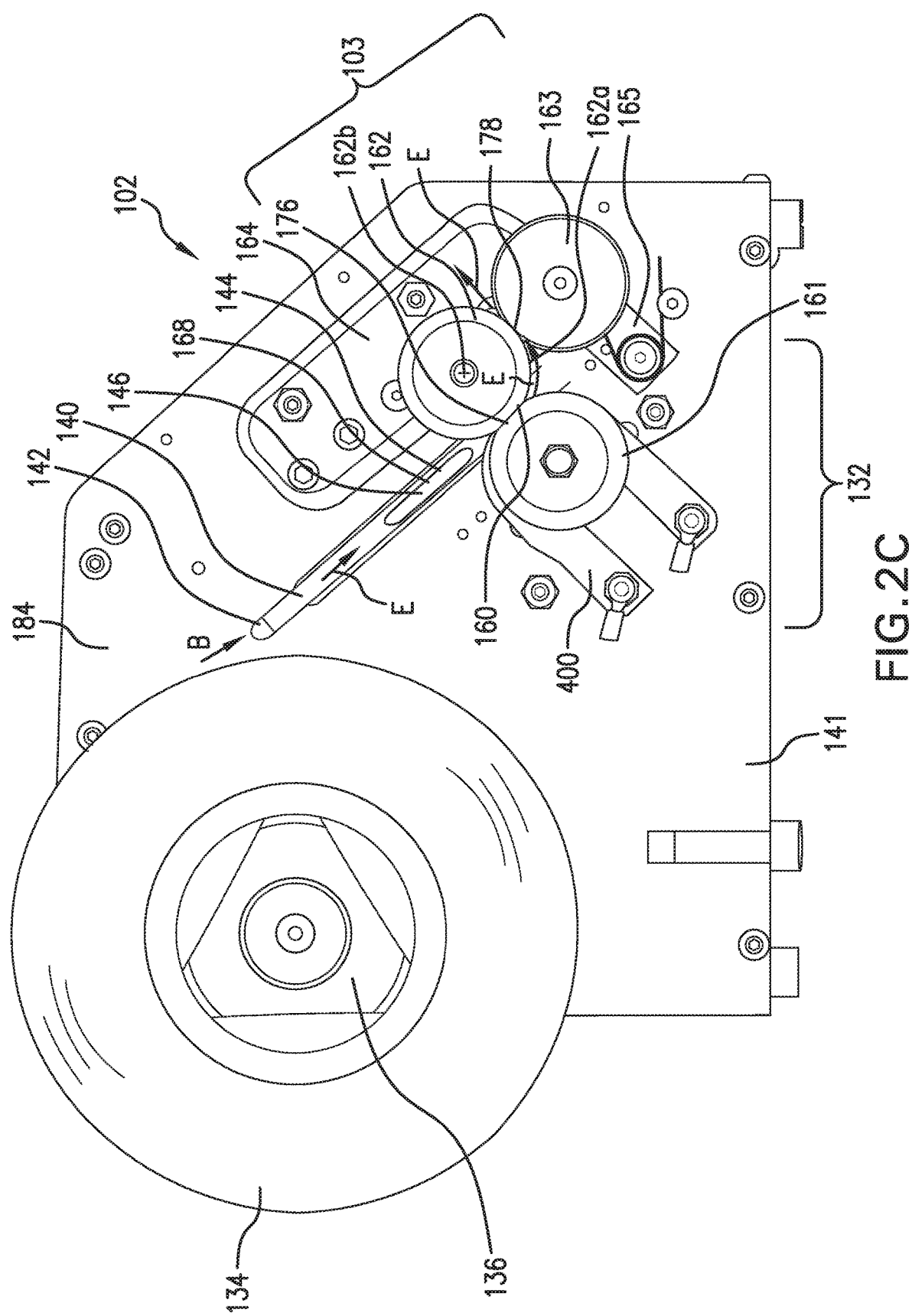

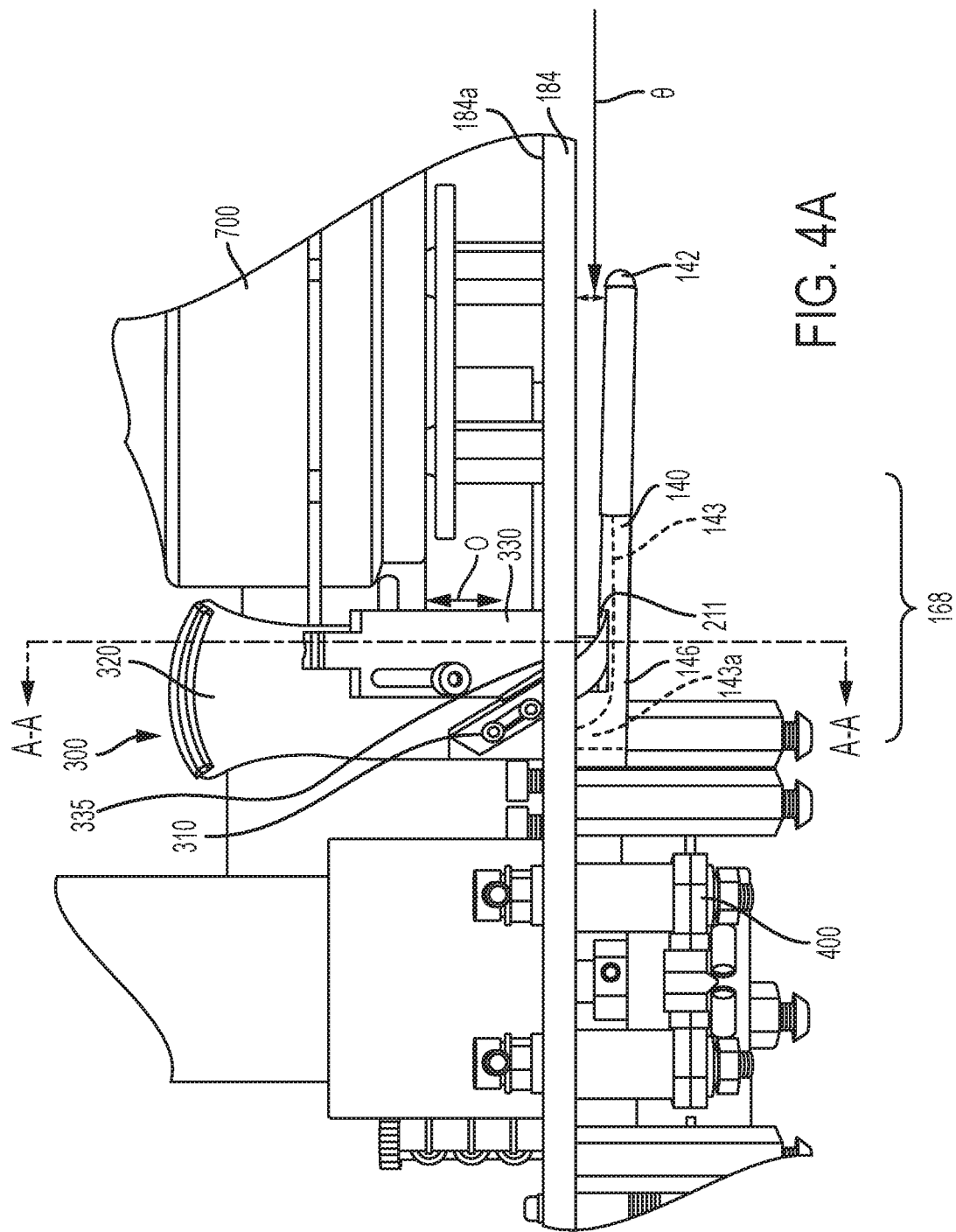

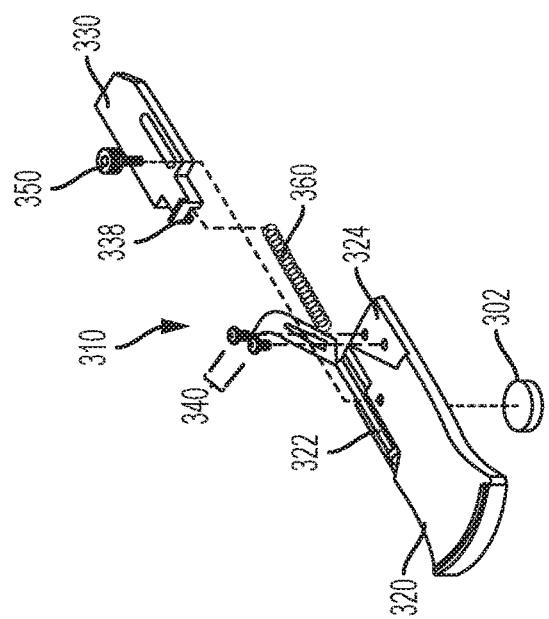
FIG. 4E
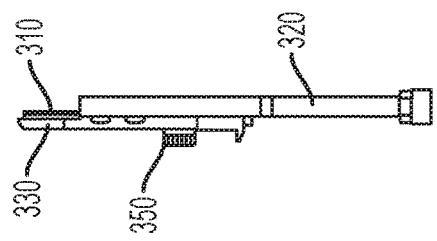
FIG. 4J
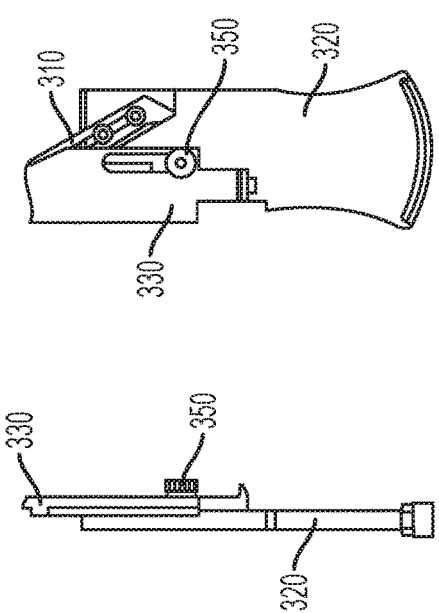
FIG. 4I
FIG. 4H
FIG. 4G
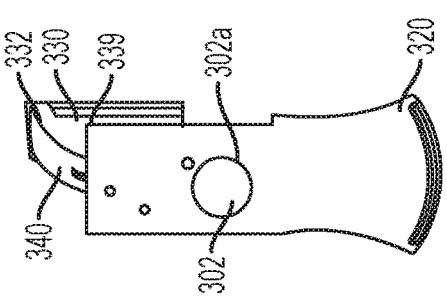
FIG. 4F

BLADE HOLDER FOR INFLATION AND SEALING DEVICE

CROSS REFERENCE TO RELATED APPLICATION

This Application claims priority to U.S. Provisional Patent Application No. 62/314,186, entitled "Blade Holder for Inflation and Sealing Device" and filed on Mar. 28, 2016, which is herein incorporated by reference in its entirety.

TECHNICAL FIELD

The present disclosure relates to packaging materials. More particularly, the present disclosure is directed to devices and methods for manufacturing inflatable cushions to be used as packaging material.

BACKGROUND

A variety of inflated cushions are known for sundry packaging applications. For example, inflated cushions are often used as void-fill packaging in a manner similar to or in place of foam peanuts, crumpled paper, and similar products. Also for example, inflated cushions are often used as protective packaging in place of molded or extruded packaging components. Generally, inflated cushions are formed from films having two plies that are joined together by seals. The seals can be formed simultaneously with inflation, so as to capture air therein, or prior to inflation to define a film configuration having inflatable chambers. The inflatable chambers can be inflated with air or another gas and thereafter sealed to inhibit or prevent release of the air or gas.

Some devices for inflating and sealing the films have a nozzle that is inserted into a tubular channel to inflate the cushions. The film extending around the nozzle is cut to open the channel and allow the film to come off of from the nozzle. In some known machines, the blade is replaceable, such as in U.S. Patent Pub. No. 2014/0261752. Other improved solutions to blade replacement safety and ease are desirable.

SUMMARY

In accordance with various embodiments, an inflatable-cushion inflation and sealing device is provided. The inflatable-cushion inflation and sealing device includes a fluid conduit configured for directing a fluid to a nozzle configured for being received within a channel between first and second overlapping film plies and directing the fluid in between the plies to form one or more cushions. The nozzle is located on one side of a blocking element. The inflatable-cushion inflation and sealing device includes a drive mechanism configured to drive the film plies over the nozzle. The inflatable-cushion inflation and sealing device also includes a cutting member. The cutting member includes a blade holder located on the other side of the blocking element. The cutting member also includes a blade mounted on the blade holder. The blade includes a cutting edge that extends across the blocking element such that as the drive mechanism drives the film plies over the nozzle and the drive mechanism also drives the film plies across the blade operably cutting the film plies. The cutting member also includes a blade guard having a safety position covering the cutting edge and a working position in which the blade cutting edge is exposed when the blade is across the blocking element placing the blade guard in contact with the blocking element. The blade guard is associated with the blade holder and blade such that removing the blade holder from the inflation and sealing device automatically moves the blade guard out of contact with the blocking element and allows the blade guard to transition so the blade is in the safety position.

In accordance with various embodiments, the blade holder is a tray located on one side of the blocking element with a portion of the blade extending past the blocking element positioned in the working position of the blade. The blade guard is mounted on the tray movable between the working and safety positions. The tray and the blade guard are slideably connected with respect to one another such that the blade guard extends past the first end of the tray, covering the blade, in the safety position. The slideable connection between the tray and blade guard defines a linear path of the blade guard between the safety and working positions. The cutting member includes a biasing element connected between the tray and the blade guard to bias the blade guard to the safety position. At least one of the tray or the blade guard includes a guide element suitable to form a rectilinear motion between the tray and the blade guard.

In accordance with various embodiments, the tray includes a grip portion on a second end of the tray opposite the first end of the tray. The grip portion includes a ridge protruding from the tray suitable to engage a user's fingers such that a user can apply a sufficient force to remove the tray from the flexible structure inflation device. The grip portion includes a convexly curved profile on the second end of the tray. The blocking element is the housing plate and the portion of the blade passes through a hole in the housing plate such that when the cutting assembly is located in the inflation and sealing device the blade guard is positioned in the working position because the housing plate compresses the biasing member. The blade guard includes a retraction grip positioned on an end of the blade guard opposite the blade guard recess.

In accordance with various embodiments, the blade holder includes a blade recess that holds the blade in a fixed position that limits rotation of the blade as the film plies press against the blade. The blade cutting edge generally faces the blade holder. The cutting edge has a curved profile that is concave such that the cutting edge faces generally toward the blade holder and in an upstream direction engaging the film plies as the film plies move downstream. The blade includes a tip facing in an upstream direction of the film plies. The blade is a medical scalpel blade.

The tray includes a locating element positioned to removably attach the tray to an inflation assembly while holding the cutting member in an operative position adjacent the inflation assembly to cut the film plies passing over the inflation assembly. The locating element is a tray magnet and an inflation assembly magnet that are positioned such that they mate together when the cutting assembly is installed into the inflation and sealing device. The force between the tray magnet and the inflation assembly magnet is sufficiently strong to prevent the biasing element from separating the tray magnet and the inflation and sealing assembly magnet. The blade tip is positioned in a recess within the inflation nozzle to cut the inflation channel open to allow the first and second plies to move off from the inflation nozzle.

BRIEF DESCRIPTION OF THE DRAWINGS

FIG. 1 is a top view of an uninflated material web according to an embodiment;

FIG. 2A-D is a perspective view, front view with covers, front view without covers, and side view, respectively, of the inflation and sealing device in accordance with a first embodiment;

FIG. 4A is a detailed top view without covers of the inflation and sealing assembly in accordance with various embodiments;

FIG. 4E is an exploded perspective view of an cutting assembly in accordance with various embodiments;

FIG. 4F-J, is an cross-sectional view, a bottom view, a side view, a top view and a side view, respectively, of cutting assembly in accordance with various embodiments;

DETAILED DESCRIPTION

Figure 2A:
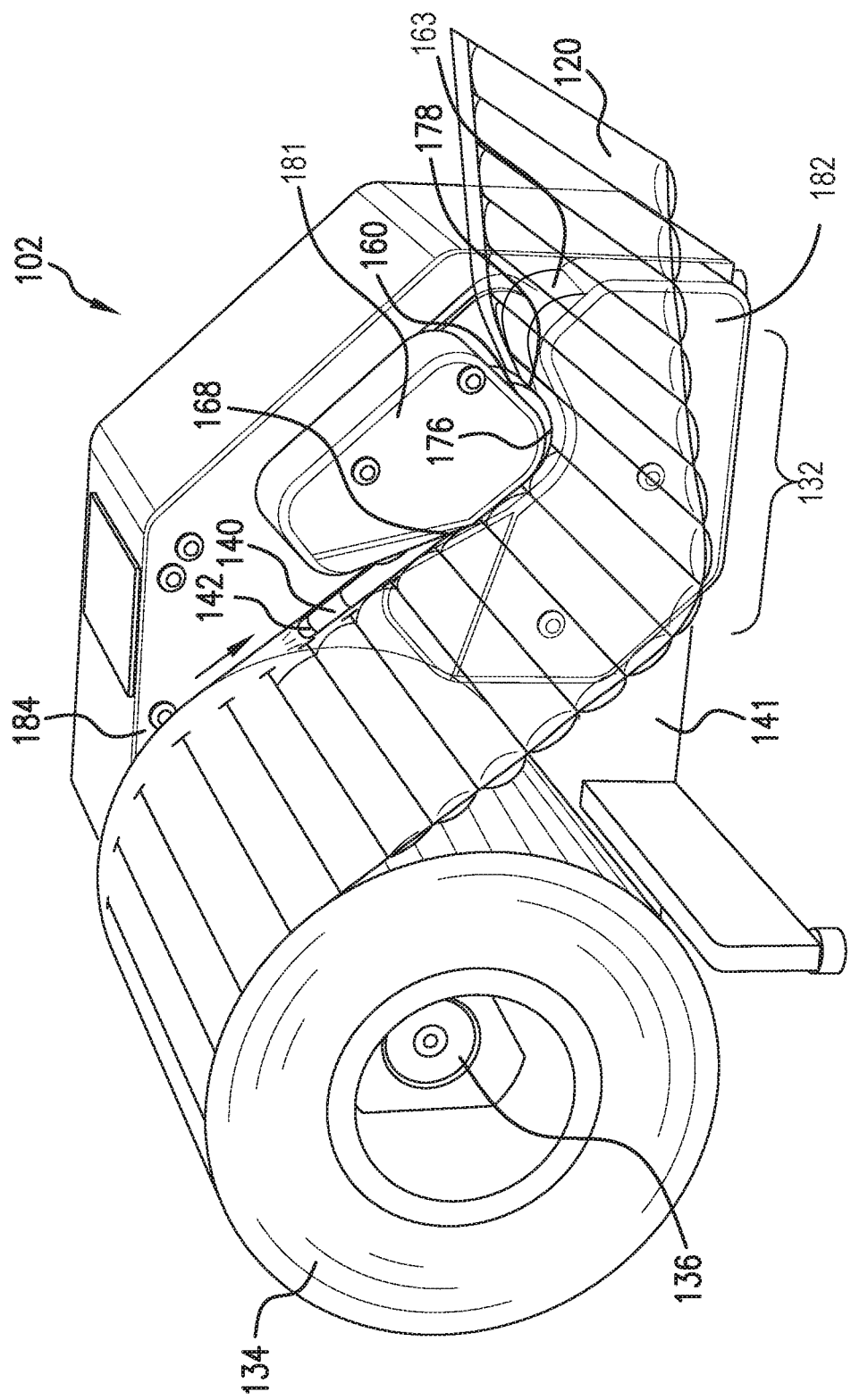
Figure 2B:
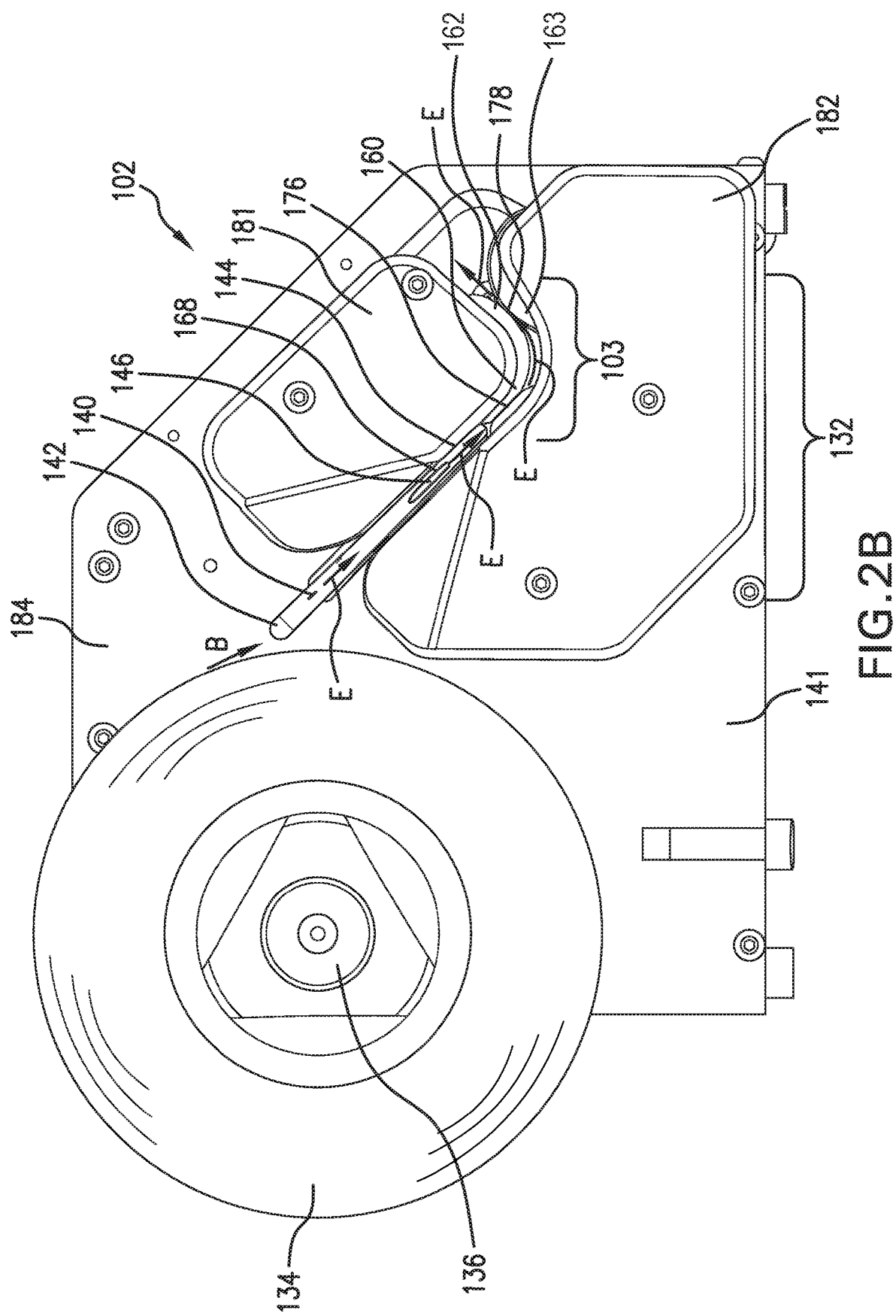

The present disclosure is related to protective packaging and systems and methods for converting uninflated material into inflated cushions that may be used as cushioning or protection for packaging and shipping goods.

As shown in FIG. 1, a multi-ply flexible structure 100 for inflatable cushions is provided. The flexible structure 100 includes a first film ply 105 having a first longitudinal edge 102 and a second longitudinal edge 104, and a second film ply 107 having a first longitudinal edge 106 and a second longitudinal edge 108. The second ply 107 is aligned to be over lapping and can be generally coextensive with the first ply 105, i.e., at least respective first longitudinal edges 102, 106 are aligned with each other and/or second longitudinal edges 104, 108 are aligned with each other. In some embodiments, the plies can be partially overlapping with inflatable areas in the region of overlap.

FIG. 1 illustrates a top view of the flexible structure 100 having first and second plies 105, 107 joined to define a first longitudinal edge 110 and a second longitudinal edge 112 of the film 100. The first and second plies 105, 107 can be formed from a single sheet of flexible structure 100 material, a flattened tube of flexible structure 100 with one edge has a slit or is open, or two sheets of flexible structure 100. For example, the first and second plies 105, 107 can include a single sheet of flexible structure 100 that is folded to define the joined second edges 104, 108 (e.g., "c-fold film"). Alternatively, for example, the first and second plies 105, 107 can include a tube of flexible structure (e.g., a flatten tube) that is slit along the aligned first longitudinal edges 102, 106. Also, for example, the first and second plies 105, 107 can include two independent sheets of flexible structure joined, sealed, or otherwise attached together along the aligned second edges 104, 108. Together the sealed plies form a web of material which is used herein also as the flexible structure 100.

The flexible structure 100 can be formed from any of a variety of web materials known to those of ordinary skill in the art. Such web materials include, but are not limited to, ethylene vinyl acetates (EVAs), metallocenes, polyethylene resins such as low density polyethylene (LDPE), linear low density polyethylene (LLDPE), and high density polyethylene (HDPE), and blends thereof. Other materials and constructions can be used. The disclosed flexible structure 100 can be rolled on a hollow tube, a solid core, or folded in a fan folded box, or in another desired form for storage and shipment.

As shown in FIG. 1, the flexible structure 100 can include a series of transverse seals 118 disposed along the longitudinal extent of the flexible structure 100. Each transverse seal 118 extends from the longitudinal edge 112 towards the inflation channel 114, and in the embodiment shown, toward the first longitudinal edge 110. Each transverse seal 118 has a first end 122 proximate the second longitudinal edge 112 and a second end 124 spaced a transverse dimension d from the first longitudinal edge 110 of the film 110. A chamber 120 is defined within a boundary formed by the longitudinal seal 112 and pair of adjacent transverse seals 118.

Each transverse seal 118 embodied in FIG. 1 is substantially straight and extends substantially perpendicular to the second longitudinal edge 112. It is appreciated, however, that other arrangements of the transverse seals 118 are also possible. For example, in some embodiments, the transverse seals 118 have undulating or zigzag patterns.

The transverse seals 118 as well as the sealed longitudinal edges 110, 112 can be formed from any of a variety of techniques known to those of ordinary skill in the art. Such techniques include, but are not limited to, adhesion, friction, welding, fusion, heat sealing, laser sealing, and ultrasonic welding.

An inflation region, such as a closed passageway, which can be a longitudinal inflation channel 114, can be provided. The longitudinal inflation channel 114, as shown in FIG. 1, is disposed between the second end 124 of the transverse seals 118 and the first longitudinal edge 110 of the film. Preferably, the longitudinal inflation channel 114 extends longitudinally along the longitudinal side 110 and an inflation opening 116 is disposed on at least one end of the longitudinal inflation channel 114. The longitudinal inflation channel 114 has a transverse width D. In the preferred embodiment, the transverse width D is substantially the same distance as the transverse dimension d between the longitudinal edge 101 and second ends 124. It is appreciated, however, that in other configurations, other suitable transverse width D sizes can be used.

The second longitudinal edge 112 and transverse seals 118 cooperatively define boundaries of inflatable chambers 120. As shown in FIG. 1, each inflatable chamber 120 is in fluid communication with the longitudinal inflation channel 114 via a mouth 125 opening towards the longitudinal inflation channel 114, thus permitting inflation of the inflatable chambers 120 as further described herein.

In one preferred embodiment, the transverse seals 118 further comprise of notches 128 that extend toward the inflatable chambers 120. As shown in FIG. 1, opposing notches 128 are aligned longitudinally along adjacent pairs of transverse seals 118 to define a plurality of chamber portions 130 within the inflatable chambers 120. The notches 118 create bendable lines that increase the flexibility of flexible structure 100 that can be easily bent or folded.

Such flexibility allows for the film 100 to wrap around regular and irregular shaped objects. The chamber portions 130 are in fluid communication with adjacent chamber portions 130 as well as with the inflation channel 114.

A series of lines of weaknesses 126 is disposed along the longitudinal extent of the film and extends transversely across the first and second plies of the film 100. Each transverse line of weakness 126 extends from the second longitudinal edge 112 and towards the first longitudinal edge 110. Each transverse line of weakness 126 in the flexible structure 100 is disposed between a pair of adjacent chambers 120. Preferably, each line of weakness 126 is disposed between two adjacent transverse seals 118 and between two adjacent chambers 120, as depicted in FIG. 1. The transverse lines of weakness 126 facilitate separation of adjacent inflatable cushions 120.

The transverse lines of weakness 126 can include a variety of lines of weakness known by those of ordinary skill in the art. For example, in some embodiments, the transverse lines of weakness 126 include rows of perforations, in which a row of perforations includes alternating lands and slits spaced along the transverse extent of the row. The lands and slits can occur at regular or irregular intervals along the transverse extent of the row. Alternatively, for example, in some embodiments, the transverse lines of weakness 126 include score lines or the like formed in the flexible structure.

The transverse lines of weakness 126 can be formed from a variety of techniques known to those of ordinary skill in the art. Such techniques include, but are not limited to, cutting (e.g., techniques that use a cutting or toothed element, such as a bar, blade, block, roller, wheel, or the like) and/or scoring (e.g., techniques that reduce the strength or thickness of material in the first and second plies, such as electro magnetic (e.g., laser) scoring and mechanical scoring).

Preferably, the transverse width 129 of the inflatable chamber 120 is 3" up to about 40", more preferably about 6" up to about 30" wide, and most preferably about 12". The longitudinal length 127 between weakened areas 126 can be at least about 2" up to about 30", more preferably at least about 5" up to about 20", and most preferably at least about 6" up to about 10". In addition, the inflated heights of each inflated chamber 120 can be at least about 1" up to about 3", and most preferably about 6". It is appreciated that other suitable dimensions can be used.

Turning now to FIGS. 2A-3C, an inflation and sealing device 102 for converting the flexible structure 100 of uninflated material into a series of inflated pillows or cushions 120 is provided. As shown in FIG. 2A, the uninflated flexible structure 100 can be a roll of material 134 provided on a roll axle 136. The roll axle 136 accommodates the center of the roll of web material 134. Alternative structures can be used to support the roll, such as a tray, fixed spindle or multiple rollers.

The flexible structure 100 is pulled by a drive mechanism. In some embodiments, intermediate members such as guide rollers can be positioned between roll 134 and the drive mechanism. For example, the guide roller can extend generally perpendicularly from a housing 141. The guide roller can be positioned to guide the flexible structure 100 away from the roll of material 134 and along a material path "B" along which the material is processed. In one example, the guide roller may be a dancer roller which may aid in controlling the material 134, such as keeping it from sagging between an inflation nozzle 140 and roll 134. In various embodiments, the stock material may advance downstream from the stock roll of material 134 without engaging a guide roll but may instead be advanced directly into an inflation and sealing assembly 132.

To prevent or inhibit bunching up of the web material 100 as it is unwound from the roll 134, the roll axle 136 can be provided with a brake to prevent or inhibit free unwinding of the roll 134 and to assure that the roll 134 is unwound at a steady and controlled rate. However, as discussed herein, other structures may be utilized in addition to or as an alternative to use of brakes, guide rollers, or web feed mechanisms in order to guide the flexible structure 100 toward a pinch area 176 which is part of the sealing mechanism 103. As indicated, because the flexible structure 100 may sag, bunch up, drift along the guide roller 138, shift out of alignment with the pinch zone 176, alternate between tense and slack, or become subject to other variations in delivery, the inflation and sealing assembly 132 may need suitable adjustability to compensate for these variations. For example, a nozzle 140 may be at least partially flexible, allowing the nozzle 140 to adapt to the direction the flexible structure 100 approaches as the structure is fed towards and over the nozzle 140, thereby making the nozzle 140 operable to compensate for or adapt to variations in the feed angle, direction, and other variations that the flexible structure 100 encounters as it is fed towards and over the nozzle 140.

The inflation and sealing device 102 includes an inflation and sealing assembly 132. Preferably, the inflation and sealing assembly 132 is configured for continuous inflation of the flexible structure 100 as it is unraveled from the roll 134. The roll 134, preferably, comprises a plurality of chain of chambers 120 that are arranged in series. To begin manufacturing the inflated pillows from the web material 100, the inflation opening 116 of the flexible structure 100 is inserted around an inflation assembly, such as an inflation nozzle 140, and is advanced along the material path "E". In the embodiment shown in FIGS. 2A-3C, preferably, the flexible structure 100 is advanced over the inflation nozzle 140 with the chambers 120 extending transversely with respect to the inflation nozzle 140 and side outlets 146. The side outlets 146 may direct fluid in a transverse direction with respect to a nozzle base 144 into the chambers 120 to inflate the chambers 120 as the flexible structure 100 advanced along the material path "E" in a longitudinal direction. The inflated flexible structure 100 is then sealed by the sealing assembly 103 in the sealing area 164 to form a chain of inflated pillows or cushions.

The side inflation area 168 is shown as the portion of the inflation and sealing assembly along the path "E" adjacent the side outlets 146 in which air from the side outlets 146 can inflate the chambers 120. In some embodiments, the inflation area 168 is the area disposed between the inflation tip 142 and pinch area 176. The flexible structure 100 is inserted around the inflation nozzle 140 at the nozzle tip 142, which is disposed at the forward most end of the inflation nozzle 140. The inflation nozzle 140 inserts a fluid, such as pressured air, into the uninflated flexible structure 100 material through nozzle outlets, inflating the material into inflated pillows or cushions 120. The inflation nozzle 140 can include a nozzle inflation channel 143 there-through, as shown for example in FIG. 4A, that fluidly connects a fluid source, which enters at a fluid inlet 143a, with one or more nozzle outlets (e.g., side outlet 146). It is appreciated that in other configurations, the fluid can be other suitable pressured gas, foam, or liquid. The nozzle may have an elongated portion, which may include one or more of a nozzle base 144, a flexible portion 162a, and a tip 142. The elongated portion may guide the flexible structure to a pinch area 176. At the same time the nozzle may inflate the flexible structure through one or more outlets. The one or more outlets may pass from the inflation channel 143 out of one or more of the nozzle base 144 (e.g. outlet 146), the flexible portion 162a, or the tip 142. The inflation nozzle 140 may extend transversely away from the front surface of the device by an angle Θ in FIG. 4A. In one example, Angle Θ is between 0 (i.e. substantially parallel) and 4°. In a more particular example, Angle Θ is between ½ and 2°. Preferably, Angle Θ is 1¼°.

Figure 4B:
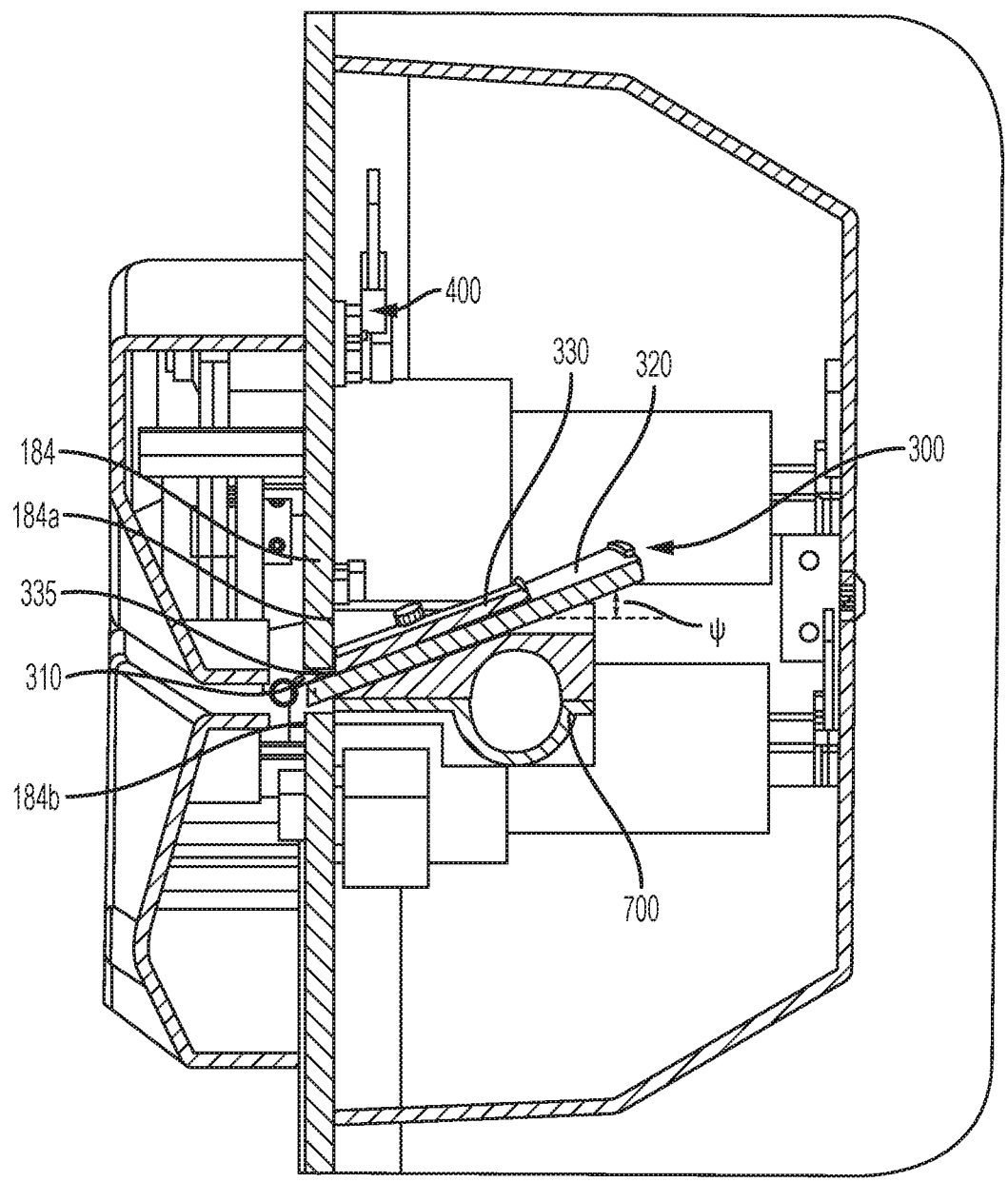
FIG. 4B is a cross-section view of the cutting assembly in accordance with various embodiments taken along A-A shown in FIG. 4A.

As shown in FIGS. 4A-B, the side outlet 146 can extend longitudinally along the nozzle base 144 toward a longitudinal distance from the inflation tip 142. In various embodiments, the side outlet 146 originates proximate, or in some configurations, overlapping, the sealer assembly such that the side outlet 146 continues to inflate the inflatable chambers 120 about right up to the time of sealing. This can maximize the amount of fluid inserted into the inflatable chambers 120 before sealing, and minimizes the amount of dead chambers, i.e., chambers that do not have sufficient amount of air. Although, in other embodiments, the slot outlet 146 can extend downstream past the entry pinch area 176 and portions of the fluid exerted out of the outlet 146 is directed into the flexible structure 100. As used herein, the terms upstream and downstream are used relative to the direction of travel of the flexible structure 100. The beginning point of the web is upstream and it flows downstream as it is inflated, sealed, cooled and removed from the inflation and sealing device.

The length of the side outlet 146 may be a slot having a length that extends a portion of the inflation nozzle 140 between the tip 142 and the entry pinch area 176. In one example, the slot length may be less than half the distance from the tip 142 to the entry pinch area 176. In another example, the slot length may be greater than half the distance from the tip 142 to the pinch area 176. In another example, the slot length may be about half of the distance from the tip 142 to the pinch area 176. The side outlet 146 can have a length that is at least about 30% of the length of the inflation nozzle 140, for example, and in some embodiments at least about 50% of the length of the inflation nozzle 140, or about 80% of the length of the inflation nozzle 140, although other relative sizes can be used. The side outlet 146 expels fluid out the lateral side of the nozzle base 144 in a transverse direction with respect to the inflation nozzle 140 through the mouth 125 of each of the chambers 120 to inflate the chambers 120 and chamber portions 130.

The flow rate of the fluid through the nozzle 140 is typically about 2 to 15 cfm, with an exemplary embodiment of about 3 to 5 or cfm. The exemplary embodiment is with a blower 700 rated at approximately 14-20 cfm. But much higher blow rates can be used, for example, when a higher flow rate fluid source is used, such as, a blower 700 with a flow rate 1100 cfm.

The nozzle 140 may further include a portion with a fixed longitudinal axis X and a portion with a movable longitudinal axis Y. The nozzle 140 may further include a flexible portion 162a which allows the nozzle 140 to be adjustable relative to the travel path "E" of the flexible structure 100. As the flexible structure 100 approaches and the inflation opening 116 engages the tip 142, the flexible core 147 may deflect and adapt to the orientation of the inflation opening 116 such that the inflation channel 114 slides more easily over the nozzle 140. Similarly, if during operation the flexible structure 100 drifts out of alignment, the flexible core 147 may deflect and adapt to the orientation of the inflation channel 114. The tip of the inflation nozzle can be used to pry open and separate the plies in an inflation channel at the tip as the material is forced over the tip. For example, when the web is pulled over traditional inflation nozzles, the tip of the traditional inflation nozzles forces the plies to separate from each other A longitudinal outlet may be provided in addition to or in the absence of the lateral outlet, such as side outlet 146, which may be downstream of the longitudinal outlet and along the longitudinal side of the nozzle wall of the nozzle base 144 of the inflation nozzle 140.

Figure 2D:
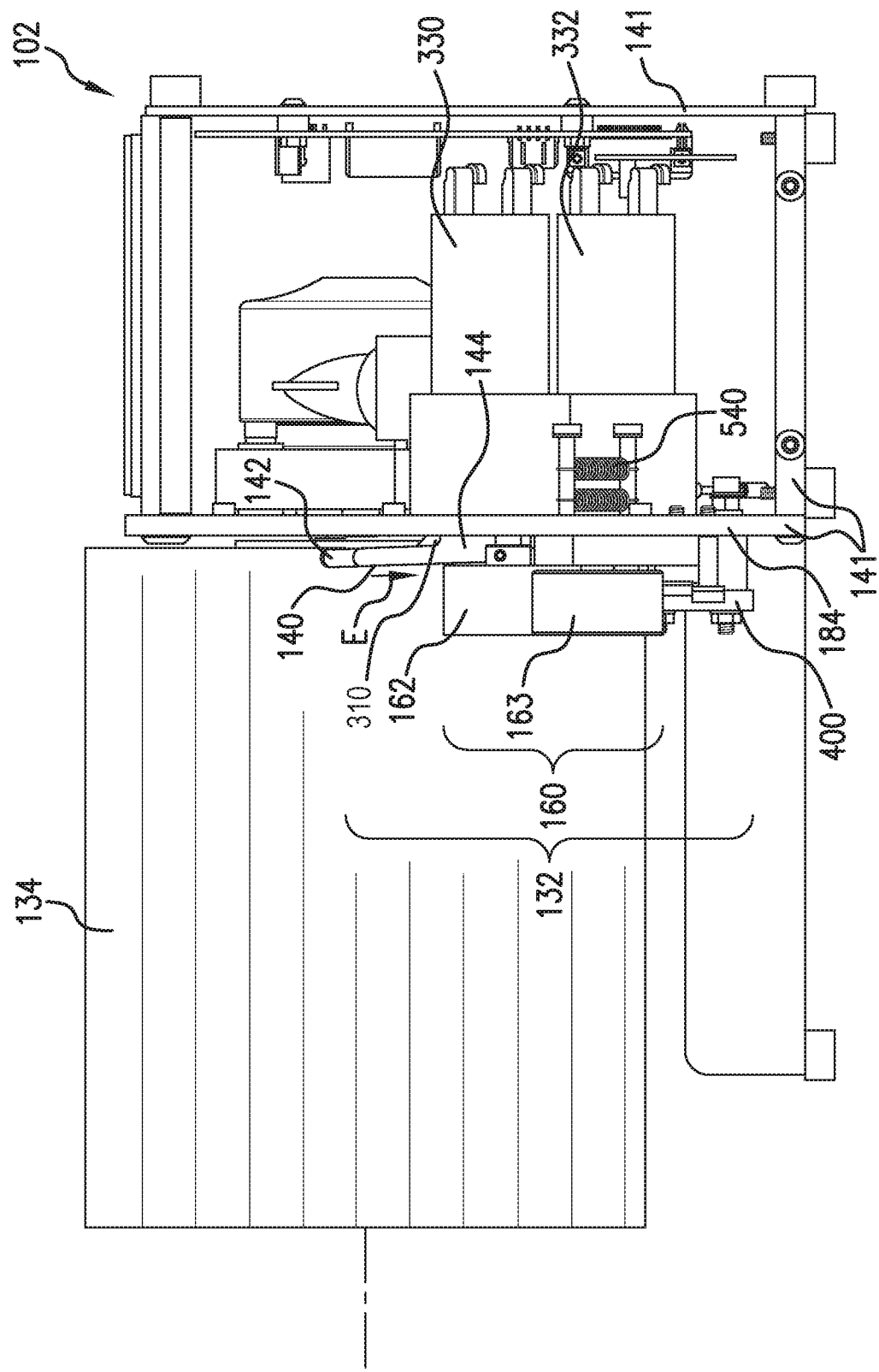

FIGS. 2D and 4B illustrate side views of various embodiments of the inflation and sealing assembly 132. As shown, the fluid source can be disposed behind a housing wall, such as a housing plate 184, or other structural support for the nozzle and sealing assemblies, and preferably behind the inflation nozzle 140. The housing plate 184 includes a sealing and inflation assembly opening 184b as shown in FIG. 4B. The fluid source is connected to and feeds the fluid inflation nozzle conduit 143. The flexible structure 100 is fed over the inflation nozzle 140, which directs the web to the inflation and sealing assembly 132.

While various examples are described herein and shown in the FIGS. 2A-4D, it should be appreciated that these examples should not be limiting and that the nozzle 140 and inflation assembly may be configured in accordance with any known embodiments or developed embodiments that may benefit from the disclosure herein as a person of ordinary skill in the art could apply based on the disclosure herein.

In accordance with various embodiments, the sealing assembly 132 includes a drive mechanism 160. The flexible structure 100 is advanced or driven through the inflation and sealing assembly 132 by the drive mechanism 160. The drive mechanism 160 includes one or more devices operable to motivate the flexible structure through the system. Specifically, the drive mechanism 160 drives the flexible structure 100 until it is received on the nozzle and then along the nozzle until the flexible structure 100 is cut by the cutting mechanism. For example, the drive mechanism includes one or more motor driven rollers operable to drive the flexible material 100 in a downstream direction along a material path "E". One or more of the rollers or drums are connected to the drive motor such that the one or more rollers drive the system. In some examples this is done without a belt contacting the flexible structure. In one example, the entire system is beltless. In another example, the system has a belt on drive elements that do not come into contact with the flexible structure 100. In another example, the system has a belt on some drive elements but not others. In other example, the system may have belts interwoven throughout the rollers allowing the material to be driven through the system by the belts. For example, U.S. Pat. No. 8,128,770 discloses a system that utilizes belts and rollers to control the inflation and sealing of cushions and the disclosure provided herein may be utilized with such a system.

In accordance with various embodiments, the inflation and sealing device 102 may include one or more covers (e.g. 181 and 182) over the inflation and sealing assembly 132. The covers (e.g. 181 and 182) can be operable to redirect the web after the web exits the second pinch area 178. For example, the covers include a deflection surface 183 that contacts the flexible material 100 as it exits the pinch area 178 and separates the flexible material 100 from the compression elements 162 and 163 redirecting the flexible material 100 in any desired direction. The cover may be a harder material than the rollers and sufficiently smooth and continuous to have relatively little engagement or adhering tendency with the flexible material 100.

Figure 3A:
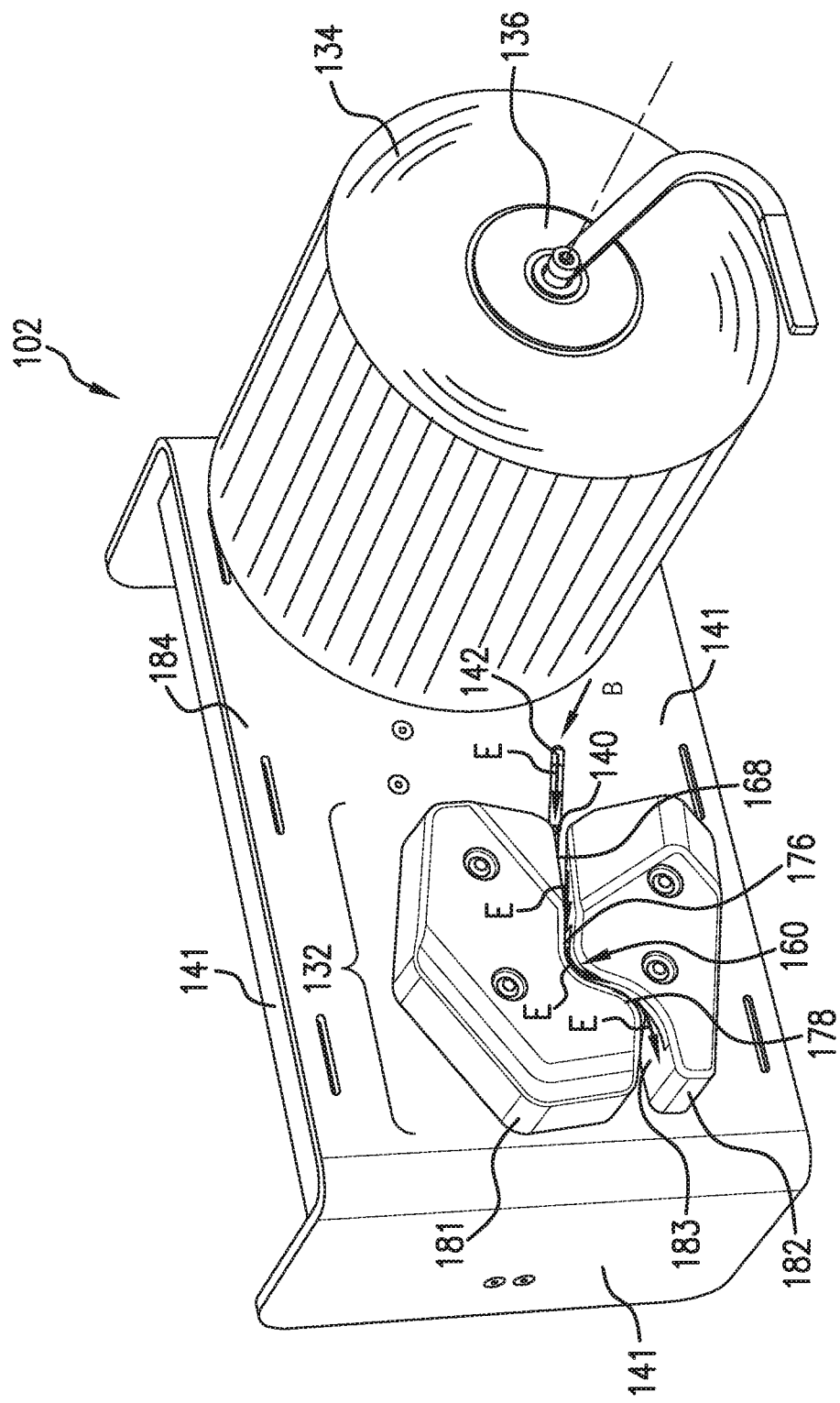
FIGS. 3A-C is a perspective view, front view with covers, and front view without covers, respectively, of the inflation and sealing device in accordance with a second embodiment.
Figure 3B:
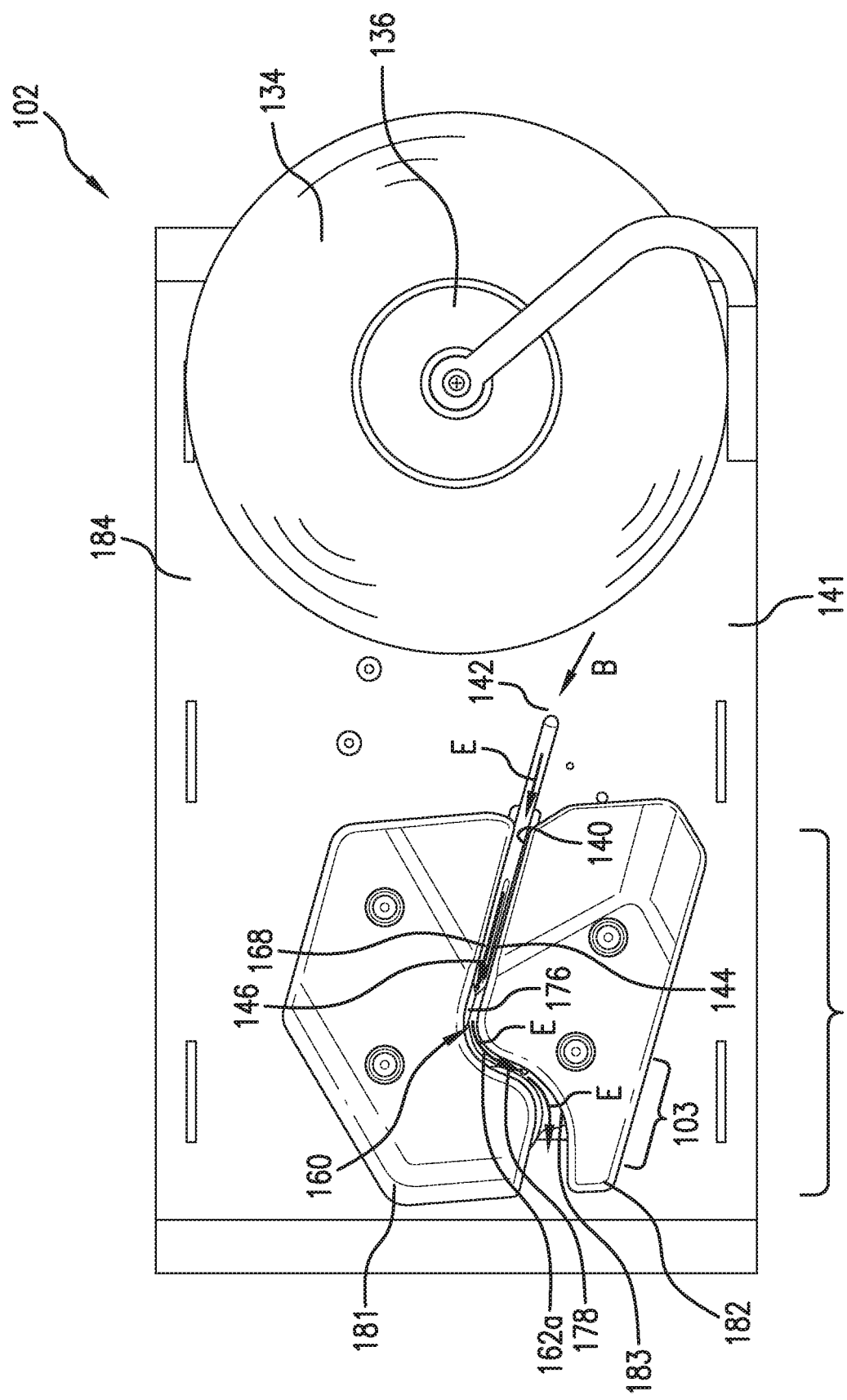
Figure 3C:
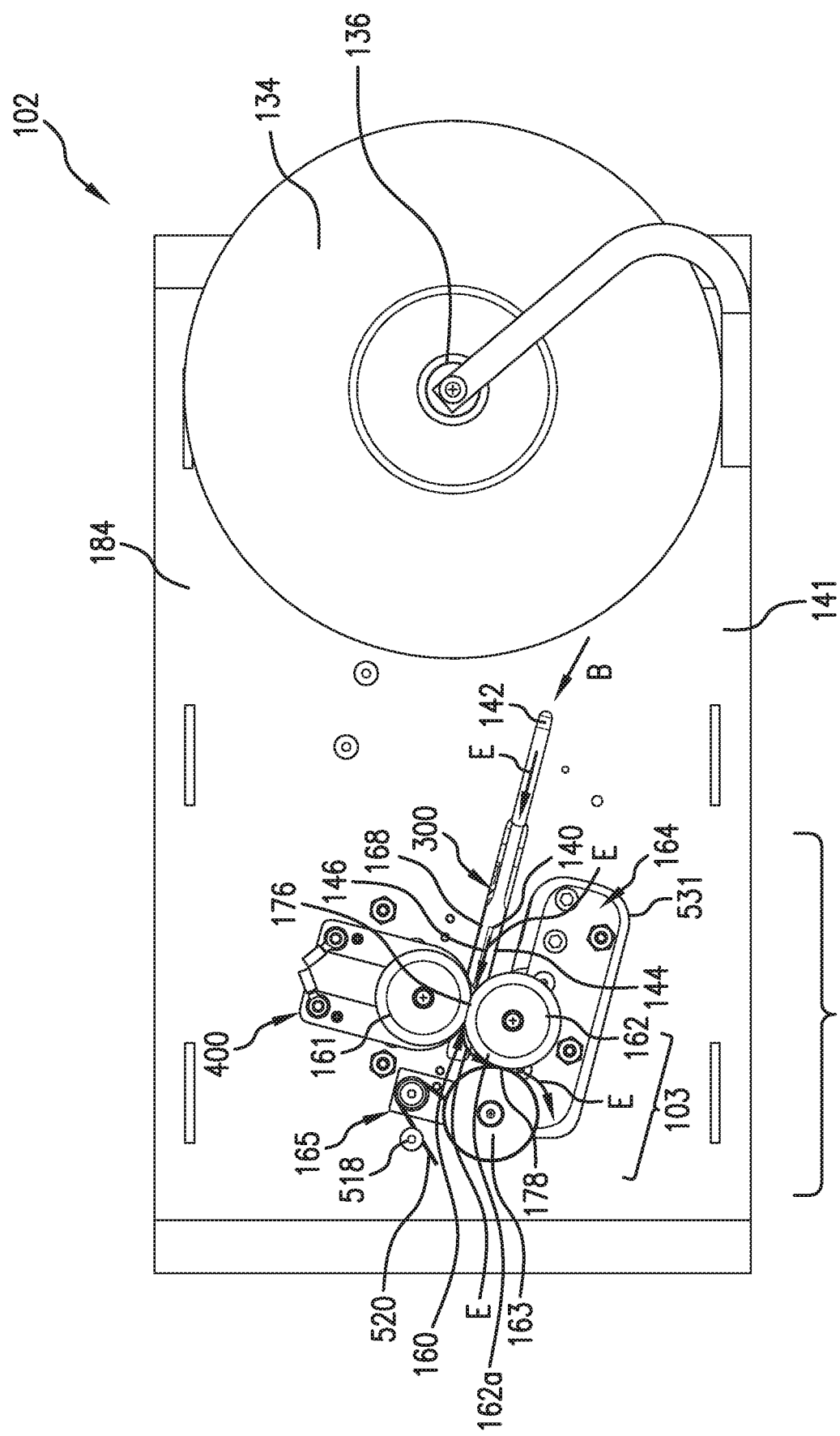

When viewed from the side, such as in FIG. 3C, in a transverse direction extending between separate portions of compression element 161, a sealing assembly is positioned transversely between the nozzle 140 and the chambers 120 being inflated to seal across each of the transverse seals. Some embodiment can have a central inflation channel, in which case a second sealing assembly and inflation outlet may be provided on the opposite side of the nozzle. Other known placement of the web and lateral positioning of the inflation nozzle and sealing assembly can be used. In accordance with various embodiments, the sealing assembly is a heating assembly 400 suitable to heat the plies together and seal them. In some embodiments, there is no sealing assembly but instead the cushions are provided with valves sufficient to hold the fluid within the chamber.

In accordance with various embodiments, the heating assembly 400 can be stationary or movable. In one example, the heating assembly 400 is attached to the housing plate 184. The heating assembly 400 is positioned adjacent to one or more traction members, such as roller portions of 161, which are driven via a motor or similar motivational source. In one example, the heating assembly can be a part of a roller movable with the roller. After inflation, the flexible structure 100 is advanced along the material path "E" towards the pinch area 176 where it enters the sealing assembly 103. The pinch area 176 is disposed between adjacent compression elements 161 and 162. The pinch area 176 is the region in which the first and second plies 105,107 are pressed together or pinched to prevent fluid from escaping the chambers 120 and to facilitate sealing by the heating assembly 400.

The heating assembly 400 may include a heating element disposed adjacent to the pinch location to heat the pinch area 176. While in the various embodiments disclosed herein the compression elements adjacent to the pinch area 176 may roll, in one embodiment, the heating element is a stationary heating element. However, in other embodiments, the heating element may move with the compression elements, be stationary with the compression elements, or move relative to the movement of the compression elements. For example, the heating element may form part of a heated drum. As indicated above, the pinch area 176 is the area where the compression elements 161 and 162 are in contact with each other or with the flexible material 100. The compression elements 161 and 162 have sufficient tension to tightly pinch or press the plies 105,107 together. This compression may also bias the plies 105, 107 against the heating assembly 400. During, before, or after being fed through the pinch area 176, the first and second plies 105,107 are sealed together by the heating assembly 400 and exit the pinch area 176. The heating element can be formed of thermocouples, which melt, fuse, join, bind, or unite together the two plies 105,107, or other types of welding or sealing elements.

After being sealed, the first and second plies 105,107 are cooled allowing the seal to harden by rolling the sealed first and second plies 105,107 around a cooling element. The cooling element may act as a heat sink or may provide a sufficient cooling time for the heat to dissipate into the air. In accordance with various embodiments, the cooling element is one or more of the compression elements 161, 162.

Preferably, the flexible structure 100 is continuously advanced through the sealing assembly 103 along the material path "E" and past the heating assembly 400 at an area 176 to form a continuous longitudinal seal 170 along the flexible structure 100 by sealing the first and second plies 105,107 together. The flexible structure 100 exits the pinch area 176, maintaining contact with the element 162. In the preferred embodiment, the heating assembly 400 and one or more of the compression elements 161, 162 cooperatively press or pinch the first and second plies 105,107 at the first pinch area 176 against the heating assembly 400 to seal the two plies together. The sealing assembly 103 may rely on pressure from compression element 162 against the heating assembly 400 to sufficiently press or pinch the plies 105,107 therebetween. The flexible resilient material of the compression elements 161, 162 allows for the pressure to be well controlled by the positions of the compression elements 161, 162.

In accordance with various embodiments, the inflation and sealing assembly 132 may further include a cutting assembly 300 to cut the flexible structure 100. Preferably, the cutting member is sufficient to cut the flexible structure 100 as it is moved past the edge along the material path "E". More particularly, the cutting assembly 300 may cut the first and second plies 105, 107 between the first longitudinal edge 101 and mouth 125 of the chambers. In some configurations, the cutting assembly 300 may cut the flexible structure 100 to open the inflation channel 114 of the flexible structure 100 and remove the first and second plies 105, 107 from the inflation nozzle 140. In various embodiments, the inflation channel 114 of the flexible structure can be central to the structure or in other locations. In such embodiments, the cutting assembly 300 can still be adapted to remove the inflation channel 114 from the inflation and sealing assembly, particularly the nozzle 140.

Figure 4C:
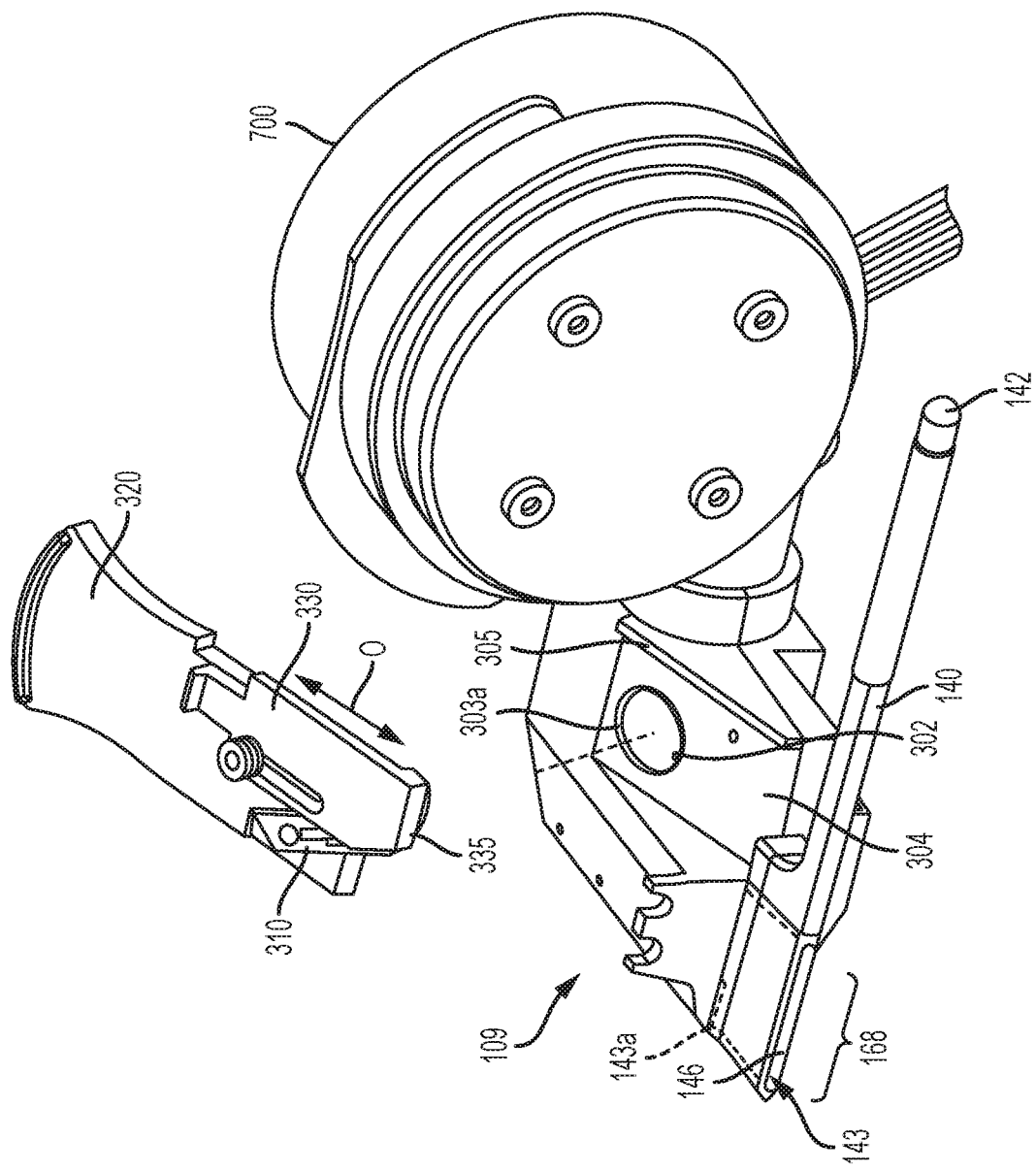
FIG. 4C is a front perspective view of a blower and cutting assembly with the cutting assembly being removed in accordance with various embodiments.
Figure 4D:
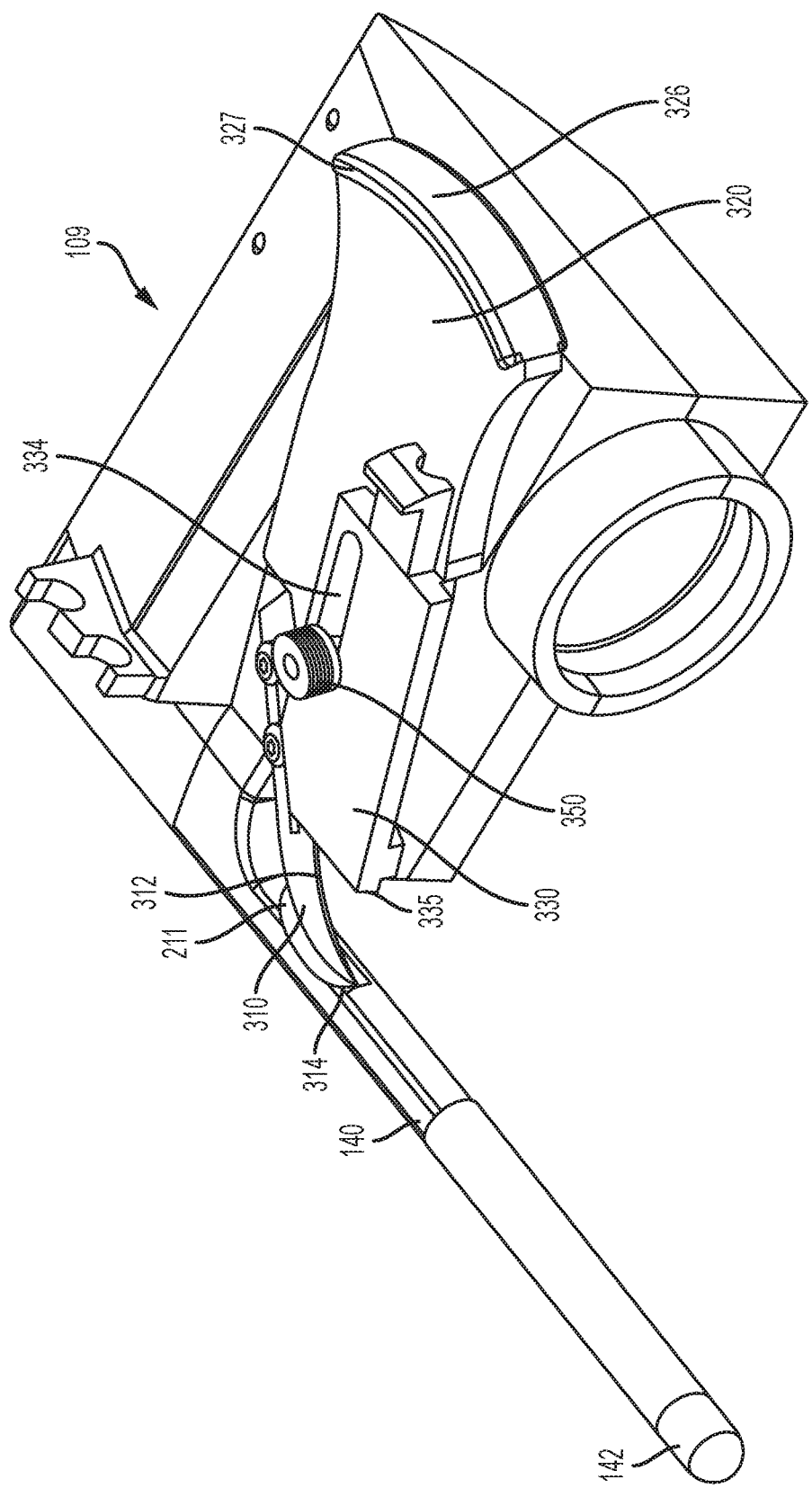
FIG. 4D is a rear perspective view of a blower and cutting assembly in accordance with various embodiments.

In according with various embodiments, examples of which are illustrated in FIGS. 4A-4M, the cutting assembly 300 is a removable assembly that allows a user to safely change the blade 310. The cutting member 300 includes a blade guard. The blade guard can by any structure suitable to hold, mount, or house the blade 310. In various embodiments as generally described herein, the blade guard is tray 320. The tray 320 holds a blade 310. Additionally, a blade guard 330 is mounted to the tray 320. In various examples, the blade 310 is automatically covered when the cutting assembly 300 is removed from the sealing assembly 132. In accordance with various embodiments, as the tray 320 is installed onto the inflation assembly 109, the blade guard 330 is automatically retracted to a retracted position, exposing the blade 310. As the tray 320 is removed from the inflation assembly 109, the blade guard 330 is automatically extended over the blade 310 into a safety position. FIG. 4A illustrates the cutting assembly from a top view with the blade guard 330 in a retracted position. FIG. 4B illustrates the cutting assembly 300 from a side cross-sectional view (as taken along the view line in FIG. 4A) with the blade guard 330 also in a retracted position. FIG. 4C shows the cutting assembly 300 in a view with the cutting assembly removed from the inflation assembly 109 and the blade guard 330 in a safety position.

Figure 4K:
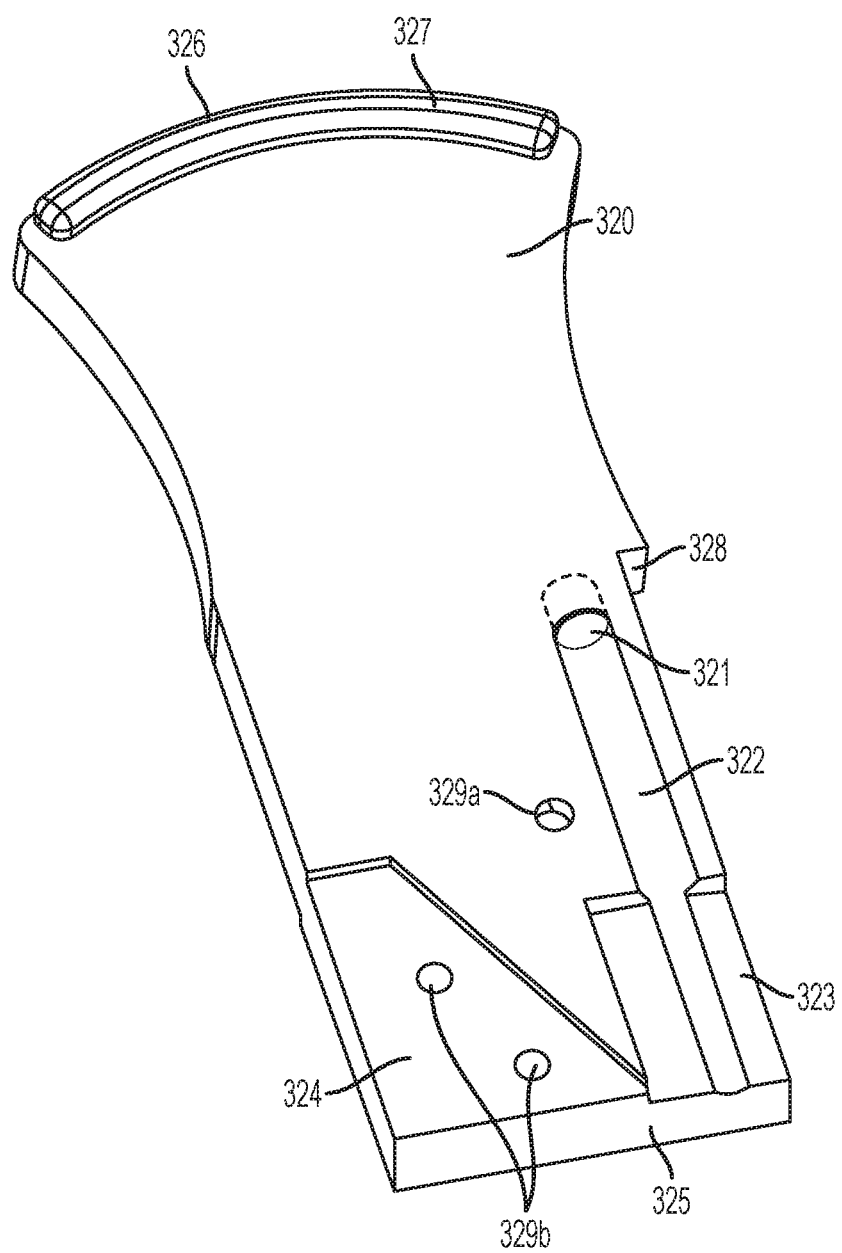
FIG. 4K is a top perspective view of a tray in accordance with various embodiments.
Figure 4L:
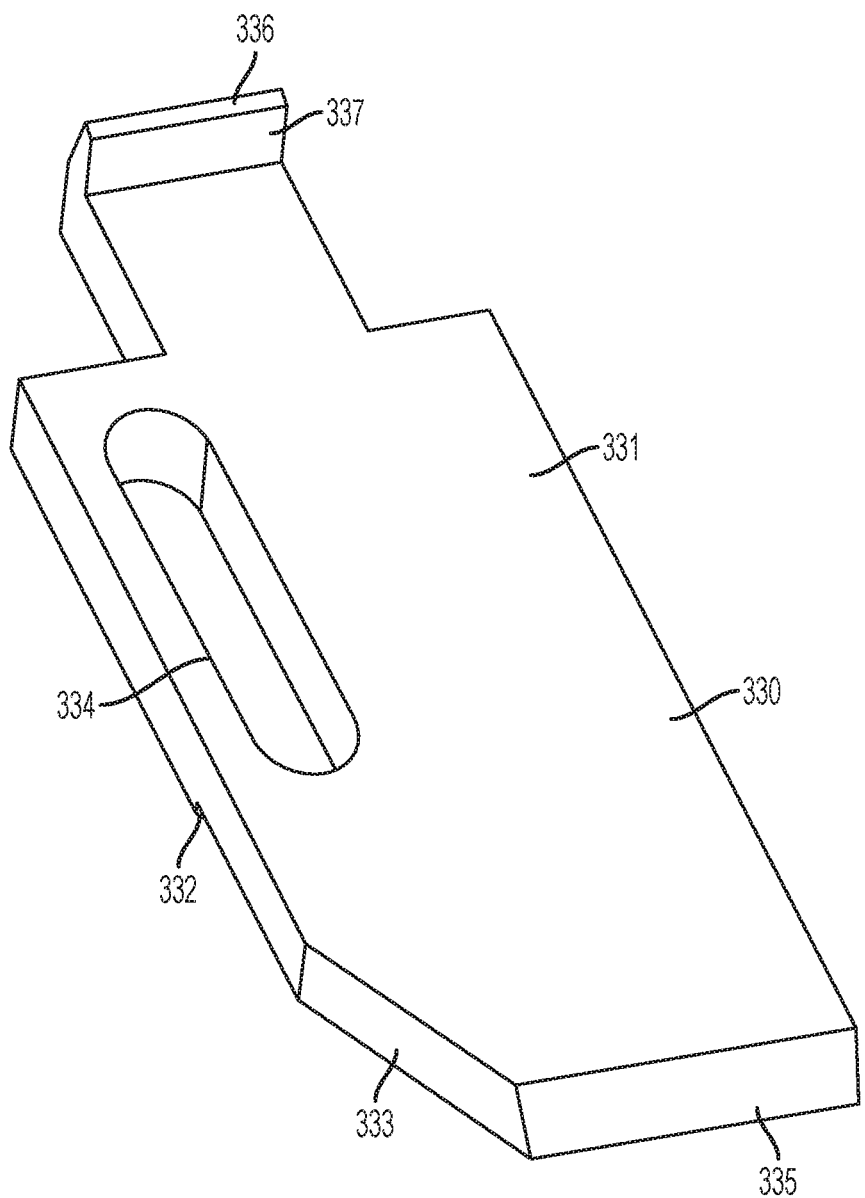
FIG. 4L is a top perspective view of a blade guard in accordance with various embodiments.
Figure 4M:
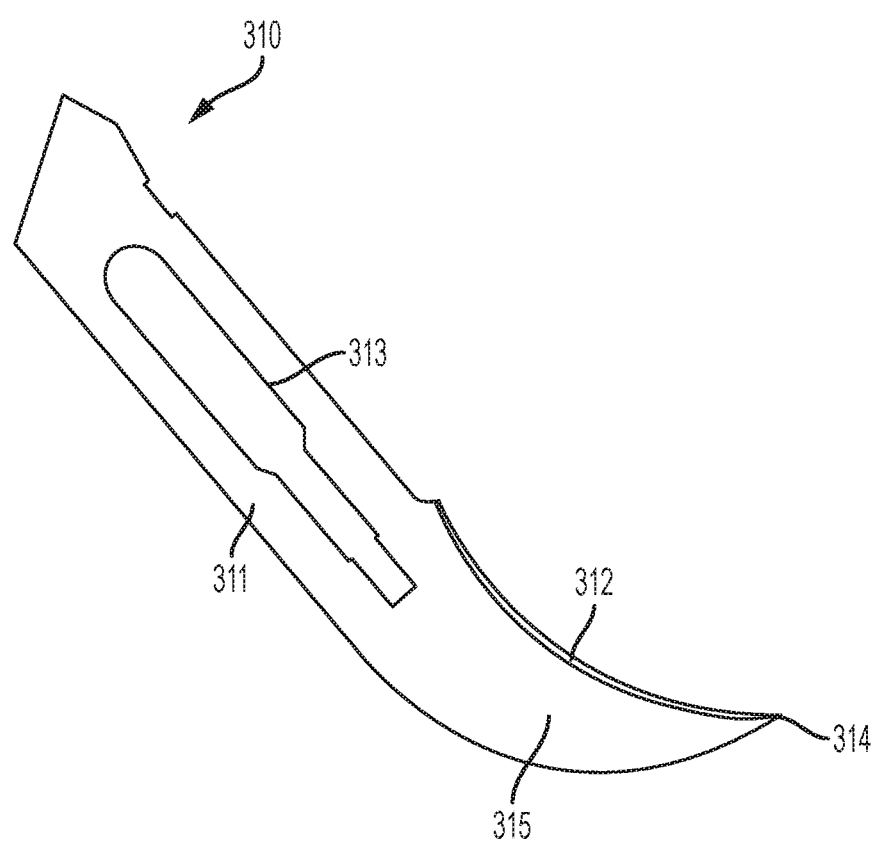
FIG. 4M is a perspective view of a knife in accordance with various embodiments.

As indicated above and in accordance with various embodiments, the cutting member 300 includes one or more of the tray 320, the blade guard 330, and the blade 310. The blade is affixed either directly or indirectly to the tray 320. In one example, the tray 320 includes a blade recess 324 (as shown in FIGS. 4E and 4K). The blade 310 is received within a recessed area 324 of the cutting tray 320. The recessed area 324 preferably includes walls to position and align the blade 310 in a fixed position within the tray 320. In one example, at least one wall defining the recessed area 324 angles the blade in an upstream direction. In various examples, the blade 310 includes one or more fastening apertures 329b, allowing the blade 310 to be removably attached to the tray 320 by fasteners 340. For example, as shown in FIG. 4M, the blade 310 includes a longitudinal slot 313 extending through the body 311. The longitudinal slot 313 is suitable to receive a fastener 340 to attach the blade 310 to the tray 320. In other embodiments, the blade 310 is attached to tray 320 by one or more fastening elements such as a snap fit, magnetic attachment, adhesive or similar types of connections either known or developed.

To protect the blade 310 and or users from the blade 310 when the cutting assembly is being removed or is removed from the system, the cutting assembly includes a blade guard 330. In accordance with various embodiments, the tray 320 and the blade guard 330 are movably connected with respect to one another. In accordance with other embodiments, the tray 320 and the blade 310 are movably connected with respect to one another. For example, as the cutting assembly 300 is being removed or is removed from the system, the blade 310 may retract to the tray 320 either on its surface. In one example, as a blade holder, the blade 310 may be retracted into a cavity within the blade holder 320, thereby protecting the blade. In such an embodiment, the blade guard 330 may be a stationary part of the blade holder 320.

In embodiments, wherein the tray 320 and the blade guard 330 are movably connected with respect to one another, the movable relationship allows the blade guard 330 to extend past the first end of the tray 320 into the safety position covering the blade 310 or allows the blade guard 330 to be retracted such that the blade guard 330 does not cover the blade 310. The movable connection between the tray 320 and the blade guard 330 can be any relationship that allows the cutting assembly to adapt between a working position with the blade guard in a retracted position suitable for cutting and a non-working position with the blade guard in a safety position suitable for protecting a user or objects from the blade 310. In one example, the movable relationship is a slideable connection between the tray 320 and blade guard 330. The slideable connection is one that allows the blade guard to slide in a rectilinear path, slide in a curvilinear path, pivot around an axis, or some combination or modification of these relationships. In accordance with various embodiments, a positioning mechanism can hold the blade guard 330 in an open position or retracted position. In another embodiment, the positioning mechanism can hold the blade guard in a closed position or safety position. In another embodiment, the positioning mechanism is a biasing element 360 that can bias the blade guard toward one position or the other.

In various examples, the tray 320 or the blade guard 330 includes a guide element suitable to maintain the defined path of motion between the tray 320 and the blade guard 330. In an example in which the defined path is a rectilinear path, the tray may include one or more guide elements. For example, the tray 320 may include a blade guard recess 323. The blade guard recess 323 can be a recessed area having one or more walls that allow a portion of the blade guard 330 to nest and or slide therein, allowing for control of the orientation of the blade guard 330. In various examples, the blade guard recess 323 is located proximal to the end of the tray 320 on which the blade 310 is mounted. For example, the blade guard 330 may have a protrusion 339 that corresponds to the blade guard recess 323, which may limit the rotation of the two components relative to one another. The tray 320 and or the blade guard 323 can also have a second or alternative guide element. In one example as shown in FIGS. 4E-4J and 4L, the blade guard 323 includes an elongated slot 334 as the second or alternative guide element. The slot 334 is sized to receive a control element 350 therein. In one example, the control element 350 is a shoulder screw. The tray 320 includes a corresponding alignment feature 329a for receiving the control element 350. In one example, the corresponding alignment feature 329a is an aperture for receiving the shoulder screw. In this example, the shoulder screw aligns and passes through the slot 334, connecting the blade guard 330 with the tray 320. The slot 334 and the recess 323 are operable to maintain a rectilinear motion between the tray 320 and the blade guard 310.

In accordance with various embodiments, the cutting assembly 300 also includes a biasing element 360 that is suitable to bias the cutting assembly into the safety position or the retracted position. In embodiments having a movable blade guard 330, the biasing element 360 biases the blade guard into the safety position or the retracted position. In embodiments having a movable blade 310, the biasing element 360 biases the blade 310 into the safety position or the retracted position.

In various examples, the biasing element 360 is positioned between the tray 320 and the blade guard 330. In a particular example, the biasing element 360 biases the blade guard 330 to the safety position. The tray 320 or the blade guard 330 has a biasing element recess positioned to capture the biasing element 360 between the tray 320 and the blade guard 330, allowing the biasing element 360 to exert a force between the tray and the blade guard. For example, tray 320 includes channel 322 that is operable to receive the biasing element 360. (See FIG. 4K.) The blade guard 330 includes channel 338 that is operable to receive the biasing element 360 therein. In various embodiments, the biasing element may be a spring, such as a compression spring. Although in other embodiments, the biasing element 360 can take the form of other resilient devices suitable to bias the blade guard into a retracted or safety position. The tray 320 and or the blade guard 330 may also include an end stop 321 suitable to capture the ends of the biasing element 360. With the biasing element 360 captured between the tray 320 and the blade guard 330, the biasing element 360 can exert a longitudinal force driving the blade guard 330 and the tray 320 apart, such that the blade guard 330 is naturally biased out over the blade 310. Thus, as the cutting assembly 300 is removed from the machine, the spring-loaded blade guard 330 slides over the top of the blade 310; this motion helps eliminate accidental contact with the blade 310. When removed from the machine, the blade 310 is covered. Installing the cutting assembly 300 into the machine and placing it in a working position, on the other hand, can overcome the bias of the blade guard 330, moving it back and exposing the blade 310 into the retracted position.

The blade 310 includes a tip 314 on the cutting end 315 of the blade 310. When the cutting assembly is installed in the inflation and sealing device, the tip of the blade inserts into an opening 211 in the air tube of nozzle 140. The tip 314 faces in the upstream direction such that as the film plies 105, 107 move downstream over the nozzle 140, the film plies 105, 107 engage the cutting edge 312 of the blade 310. In some embodiments, the film plies 105, 107 do not engage the blade tip 314 as the blade tip 314 is positioned in a recess 211. The blade tip 314 position in the recess 211 within the inflation nozzle 140 allows the cutting edge 312 to cut the inflation channel open to allow the first and second plies to move off from the inflation nozzle 140. This relationship forms a continuous cutting surface that the flexible structure 100 collides with and is cut by to minimize jamming of the flexible structure 100 on the tube as it slides along the nozzle 140 via the inflation channel formed within the flexible structure 100. The cutting edge can have different profiles, shapes, or edges for cutting the film 100. The cutting edge is any structure suitable to cut one or more of the film plies such that the flexible structure can be removed from the nozzle. In one example, the cutting edge 312 includes a curved profile. In a more particular example, the curved profile is concave. In one example, the cutting edge is a serrated edge. In some examples, the cutting edge is sharp, while in other examples the cutting edge is not sharp per se but has sufficient features to cut the film plies. In various embodiments, the cutting edge 312 faces generally toward the tray 320 and generally in an upstream direction to engage one or more of the film plies. The curved profile helps increase the useful life of the blade. As the blade 310 wears and becomes dull, the material slides further down the blade to the unused and sharper portion of the blade 310. In various examples, the blade is a standard medical scalpel blade. In the embodiment shown, the cutting edge 312 is preferably angled upward toward the inflation nozzle 140, although other configurations of the cutting edge 312 can be used.

In accordance with various embodiments, the blade guard includes a blade guard recess 332 (shown in FIG. 4G) which conforms to a profile of a cutting edge 312 of the blade. For example, a concave profile on the blade would nest within a recess 332 with one wall of the recess being convex to correspond to the concave profile of cutting edge 312. Accordingly, in the safety position, the guard recess 332 is positioned immediately adjacent to the blade cutting edge 312. When the blade guard 330 is located in its retracted position, the recess 332 is drawn back away from the cutting edge 312 so that the cutting edge 312 is operable to engage the flexible structure 100.

In accordance with various embodiments, the tray 320 includes a grip portion 327 on a second end 326 of the tray 320 opposite the first end of the tray 325. The grip portion 327 includes a ridge protruding from the tray 320 suitable to engage a user's fingers such that a user can apply a sufficient force to remove the tray from the flexible structure inflation device 102. The grip portion 327 includes a convexly curved profile on the second end 326 of the tray 320.

In accordance with various embodiments, the blade guard 330 includes a retraction grip 337. The retraction grip is positioned on an end 336 of the blade guard 330. The end 336 is on the opposite end of the blade guard relative to the blade recess 332. The retraction grip 337 may be used to retract the blade guard 330 from over the blade 310 after the cutting assembly 300 is removed from the inflation and sealing device. By using the retraction grip 337 to pull the blade guard 330 back, the blade 310 can then be removed and replaced by a new sharp blade. In one example, the retraction grip is a protrusion that extends from the body 331 of the blade guard 330 on the end of the blade guard 330 opposite the contact surface.

In accordance with various embodiments, the tray 320 is positioned such that as the cutting member 300 is placed in a working position, the blade guard 330 contacts a portion of the inflation and sealing device 102 causing the blade guard 330 to retract. For example, the tray 320 is placed in a working position proximal to a blocking element such that the blade guard 330 contacts the blocking element and is retracted. In the working position, the blade 310 extends proximal to the nozzle and the blade guard 330 is retracted exposing the blade 310. The blocking element can be any obstruction or the like that can expose the blade 310, for example by contacting and manipulating the position of blade guard 330 when installing the cutting assembly 300. In one example, the blocking element is housing plate 184. In this example, a portion of the blade 310 can pass through (e.g. a hole) or across (e.g. one edge) the plate 184, such that the blade guard 330 contacts the plate 184, with the plate 184 retracting the guard 330 into the retracted position. It may be appreciated that the blocking element can be a variety of elements suitable to contact the guard 330 and keep the guard from moving with the blade 310 as the cutting assembly is set in place. The blocking element could be a ring, a bar, an edge of a structure, a hole in a structure or any similar element.

In various embodiments, the tray 320 is positioned on a support structure 304. While the support structure 304 can be on any element of the inflation and sealing device 102 suitable to position the blade 310 relative to the nozzle 140 such that the blade operably cuts the flexible structure 100 off the nozzle 140 (i.e. the working position), as illustrated, the support structure 304 forms an upper surface of the inflation assembly 109. For example, the support structure 304 receives the tray 320 and guides the tray 320 into position adjacent to the nozzle, with the blocking element positioned between the tray 320 and the nozzle. The support structure guides the tray 320 into its position adjacent the nozzle and the blocking element. The support structure also orients the tray 320 and holds the tray 320 in position during operation of the device 102. When the tray 320 is in an operable position, the support structure 304 positions the tray 320 adjacent to the blocking member such that the blocking member contacts and holds the blade guard in position away from the blade 310. This position also allows the blade to pass across or through the blocking member so that the blade can contact the flexible structure 100 as it moves past. The support structure 304 can be configured in a variety of positions. For example, as illustrated in FIGS. 4B-C, the support structure is a surface inclined relative to the horizontal plane on which the inflation and sealing device 102 rests. As shown in FIG. 4B, the support structure 304 can be a surface position at an angle of Ψ as measured off of the horizontal. In various examples, Ψ can be less than about 70° as measured off of the horizontal in either the positive or negative direction such that the blade 310 extends either upwardly or downwardly from the tray 320. In a more particular example, Ψ is between 10° and 30° as measured off of the horizontal with the blade 310 angled in a downward direction from the tray 320. In a preferred example, Ψ is about 20° as measured off of the horizontal with the blade 310 angled in a downward direction from the tray 320. In a preferred example, Ψ is the angle that allows the support structure to mate flatly with the surface it engages, e.g. the blocking element.

The support structure 304 can also include one or more positioning features. For example, a positioning wall 305 protrudes from the support structure 304. The positioning wall 305 extends from the support structure 304 along one side of the support structure. The positioning wall 305 may engage with the tray 320 to limit rotation of the tray 320. Another example of a positioning feature that the support structure 304 includes is a retaining element 303. The retaining element 303 can be any element suitable to hold or bias the tray to a particular position and or orientation. Such retaining elements can include fasteners, fixtures, brackets or the like. In a preferred embodiment, as illustrated in FIG. 4C, the retaining element is a magnet 302. In one example of this embodiment, the magnet 302 is positioned within a recess 303a that limits the lateral movement of the magnet relative to the support structure 304. The recess 303a is sized to fit the magnet 302 and is located to engage an opposing retaining element on the tray 320 such as a ferro-magnetic material.

In accordance with various embodiments, the tray 320 corresponds to the support structure 304 having a corresponding retaining element. The tray 320 retaining element can be any element suitable to hold or bias the tray to a particular position and or orientation. Such retaining elements can include fasteners, fixtures, brackets or the like. For example, as illustrated in FIGS. 4E and 4G, the tray 320 includes a magnet 302. In one example of this embodiment, the magnet 302 is positioned within a recess 302a that limits the lateral movement of the magnet relative to the tray 320. The recess 302a is sized to fit the magnet 302 and is located to engage the opposing retaining element on the support structure 304. As illustrated, these corresponding retaining elements are magnets suitable to bias the tray 320 into place on the support structure 304. In accordance with various embodiments, the force between the tray magnet 302 and the inflation assembly magnet 303 is sufficiently strong to prevent the biasing element 360 from separating the tray magnet 302 and the inflation and sealing assembly magnet 303.

Additionally or alternatively, when the tray 320 is positioned on the support structure 304, one edge of the tray may be positioned against the positioning wall 305, further orienting the tray 320. As illustrated in FIG. 4K, the tray 320 can include a notch 328 operable to engage the positioning wall 305. It should be appreciated, however, that other forms of support, orientation, or positioning features may be used to locate the blade 310 relative to the material 100 for cutting. For example, in some embodiments, the cutting assembly including tray 320 and blade 310 can be movable relative to a fixed film.

The blade guard includes contact surface 335 positioned to engage one or more elements of the inflation and sealing device 102 when the cutting assembly is positioned within the inflation and sealing device 102. Such engagement with the contact surface 335 causes the blade guard 330 to slide to the retracted position. In accordance with various examples, the contact surface 335 is positioned such that the contact surface 335 mates substantially flatly with the one or more elements of the inflation and sealing assembly 132. In accordance with various embodiments, the contact surface 335 is not positioned orthogonal to the rectilinear path O. The position of the contact surface 335 relative to the rectilinear path O is a function of the angle of the support structure 304 relative to the surface 184a as shown in FIG. 4B. In one example, the surface 184a is perpendicular relative to the horizontal on which the inflation and sealing device 102 rests. The contact surface 335 rests flat against the surface 184a. Thus, the angle between the contact surface 335 and the support structure 304 is the complementary angle of Ψ. In various other embodiments, the contact surface 335 does not mate flatly or substantially flatly against the surface 184.

In various embodiments, the blade guard includes a chamfered side 333. The chamfered side 333 extends from the contact surface 335 back towards the other end 336 of the blade guard. The chamfered side 33 may conform to the angle between the tray 320 and the blade 310 such that when the blade guard 330 is in the safety position the chamfered side 333 generally matches the blade 310 angle as shown in FIG. 4I.

A door can be included to facilitate easy opening of the inflation and sealing device 102 when the cutting holder 190 is removed from the inflation and sealing device 102 so that a user, for example, can remove the blade 310 from the cutting tray 320.

FIGS. 4E-4M illustrate one example of the cutting member 300 assembly; but, other configurations may also be implemented as a person of ordinary skill in the art would appreciate based on the disclosure contained herein. In some embodiments, it is appreciated that a cutting tray 320 can be omitted, and other suitable mechanisms can be used to position the blade 310 adjacent the inflation nozzle 140. In various embodiments, the cutting assembly 300 may be a fixed assembly or a movable one such as those described in U.S. Patent Pub. No. 2014/0261871.

Any and all references specifically identified in the specification of the present application are expressly incorporated herein in their entirety by reference thereto. The term "about," as used herein, should generally be understood to refer to both the corresponding number and a range of numbers. Moreover, all numerical ranges herein should be understood to include each whole integer within the range.

Having described several embodiments herein, it will be recognized by those skilled in the art that various modifications, alternative constructions, and equivalents may be used. The various examples and embodiments may be employed separately or they may be mixed and matched in combination to form any iteration of the alternatives. Additionally, a number of well-known processes and elements have not been described in order to avoid unnecessarily obscuring the focus of the present disclosure. Accordingly, the above description should not be taken as limiting the scope of the invention. Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. An inflatable-cushion inflation and sealing device, comprising:
   a nozzle that is insertable into a channel in a film web and that directs a fluid between overlapping plies of the web to produce an inflated cushion;
   a cutting member having a working position, the cutting member comprising:
      a blade holder that in the working position is removably located adjacent to the nozzle and positions a cutting edge of a blade adjacent the nozzle,
      a blade guard having a safety position covering the cutting edge and being retractable from the safety position so that the blade guard exposes the cutting edge in the working position; and
      a biasing element connected between the blade holder and the blade guard to bias the blade guard to move toward the safety position, wherein the biasing element includes a spring;
   a blocking element positioned with respect to the nozzle such that the blocking element engages the blade guard as the blade holder is placed in the working position causing the blade guard to retract as a leading edge of the cutting member extends beyond the blocking element with respect to the blade guard, wherein disengagement between the blocking element and the blade guard causes the blade guard to automatically move to the safety position; and a drive mechanism that drives the film web over the nozzle across the cutting edge so that the cutting edge cuts the web, opening the channel so that the web comes off the nozzle.

2. The inflatable-cushion inflation and sealing device of claim 1, wherein the leading edge of the cutting member is the cutting edge of the blade.

3. The inflatable-cushion inflation and sealing device of claim 2, further comprising the blade, which is mounted on the blade holder.

4. The inflatable-cushion inflation and sealing device of claim 3, wherein the blade holder is a tray with the blade mounted thereon and the blade extending past a first end of the tray.

5. The inflatable-cushion inflation and sealing device of claim 4, wherein the blade guard is mounted on the tray movable between a retracted position and the safety position.

6. The inflatable-cushion inflation and sealing device of claim 4, wherein the tray and the blade guard are slideably connected with respect to one another such that the blade guard extends past the first end of the tray, covering the blade, in the safety position.

7. The inflatable-cushion inflation and sealing device of claim 6, wherein the slideable connection between the tray and blade guard defines a linear path of the blade guard between the safety and retracted positions.

8. The inflatable-cushion inflation and sealing device of claim 6, wherein at least one of the tray or the blade guard includes a guide element suitable to form a rectilinear motion between the tray and the blade guard.

9. The inflatable-cushion inflation and sealing device of claim 4, wherein the tray includes a locating element positioned to removably hold the tray in the working position.

10. The inflatable-cushion inflation and sealing device of claim 9, wherein the locating element is a tray magnet attached to the tray and an inflation assembly magnet attached to an inflation assembly which connects to the nozzle and the two magnets are positioned such that they mate together, wherein a force between the tray magnet and the inflation assembly magnet is sufficiently strong to prevent a biasing element from separating the tray magnet and the inflation and sealing assembly magnet.

11. The inflatable-cushion inflation and sealing device of claim 10, wherein a blade tip is positioned in a recess within the inflation nozzle to cut the film web open along an inflation channel formed within the film web to allow the overlapping plies to move off the inflation nozzle.

12. The inflatable-cushion inflation and sealing device of claim 2, wherein the tray includes a grip portion defined by a convexly curved ridge protruding from the tray on a second end of the tray opposite a first end of the tray suitable for retracting the tray from or placing the tray in the working position.

13. The inflatable-cushion inflation and sealing device of claim 1, wherein in the working position the blade guard remains on an opposite side of the blocking element from the nozzle.

14. The inflatable-cushion inflation and sealing device of claim 1, wherein in the working position the blade guard remains on an opposite side of the blocking element from the cutting edge.

15. The inflatable-cushion inflation and sealing device of claim 1, wherein the blade guard is associated with the blade holder such that removing the blade holder from the working position automatically causes the blade guard to move to the safety position.

16. The inflatable-cushion inflation and sealing device of claim 15, wherein the blocking element is a housing plate defining a portion of a housing and a portion of the blade passes through a hole in the housing plate such that when the cutting assembly is in the working position, the blade guard is retracted because the housing plate compresses a biasing member.

17. The inflatable-cushion inflation and sealing device of claim 16, wherein the blade includes a tip facing in an upstream direction of the film web.

18. The inflatable-cushion inflation and sealing device of claim 1, wherein the blade guard includes a retraction grip positioned on an end of the blade guard.

19. The inflatable-cushion inflation and sealing device of claim 1, wherein the blade holder includes a blade recess that holds the blade in a fixed position that limits rotation of the blade as film plies press against the blade.

20. The inflatable-cushion inflation and sealing device of claim 1, wherein the cutting edge substantially faces the blade holder.

21. The inflatable-cushion inflation and sealing device of claim 20, wherein the cutting edge has a curved profile that is concave such that the cutting edge faces substantially toward the blade holder and in an upstream direction engaging the film web as the film web moves downstream.

22. The inflatable-cushion inflation and sealing device of claim 1, further comprising a sealer configured to seal the overlapping plies together to contain the fluid within an air cushion.

23. The inflatable-cushion inflation and sealing device of claim 1, wherein the blocking element disengages the blade guard as the blade holder is removed from the working position causing the blade guard to extend over the cutting member.

24. The inflatable-cushion inflation and sealing device of claim 1, wherein the blocking element holds the blade guard in a position away from the blade when the blade holder is placed in the working position.

25. An inflatable-cushion inflation and sealing device, comprising:

a nozzle that is insertable into a channel in a film web and that directs a fluid between overlapping plies of the web to produce an inflated cushion;

a cutting member having a working position, the cutting member comprising:

a blade holder that in the working position is removably located adjacent to the nozzle and positions a cutting edge of a blade adjacent the nozzle, a blade guard having a safety position covering the cutting edge and being retractable from the safety position so that the blade guard exposes the cutting edge in the working position; and a biasing element connected between the blade holder and the blade guard to bias the blade guard to move toward the safety position;

a blocking element configured to stop movement of the blade guard with respect to the nozzle as the blade holder moves into the working position, wherein the blocking element contacts the blade guard as the blade holder is placed in the working position, such that a portion of the cutting edge passes by the blocking element, but the blocking element prevents the blade guard from passing by the blocking element as the blade holder is placed in the working position; and a drive mechanism that drives the film web over the nozzle across the cutting edge so that the cutting edge cuts the web, opening the channel so that the web comes off the nozzle.

26. The inflatable-cushion inflation and sealing device of claim 25, wherein the blocking element defines an opening through which the cutting edge passes but the blade guard does not.

27. The inflatable-cushion inflation and sealing device of claim 25, wherein the movement of the blade guard, with respect to the nozzle, abruptly stops when the blade guard comes into contact with the blocking element.

28. An inflatable-cushion inflation and sealing device, comprising:
- a nozzle that is insertable into a channel in a film web and that directs a fluid between overlapping plies of the web to produce an inflated cushion;
- a cutting member having a working position, the cutting member comprising:
  - a blade holder that in the working position is removably located adjacent to the nozzle and positions a cutting edge of a blade adjacent the nozzle,
  - a blade guard having a safety position covering the cutting edge and being retractable from the safety position so that the blade guard exposes the cutting edge in the working position; and
  - a resiliently deformable biasing element connected between the blade holder and the blade guard to bias the blade guard to move toward the safety position;
- a blocking element positioned with respect to the nozzle such that the blocking element engages the blade guard as the blade holder is placed in the working position causing the blade guard to retract as a leading edge of the cutting member extends beyond the blocking element with respect to the blade guard, wherein disengagement between the blocking element and the blade guard causes the blade guard to automatically move to the safety position; and
- a drive mechanism that drives the film web over the nozzle across the cutting edge so that the cutting edge cuts the web, opening the channel so that the web comes off the nozzle.

29. The inflatable-cushion inflation and sealing device of claim 28, wherein the resiliently deformable biasing element is configured to change its shape in response to movement of the blade holder.

* * * * *